United States Patent [19]
Dandliker et al.

[11] Patent Number: 5,919,922
[45] Date of Patent: Jul. 6, 1999

[54] FLUORESCENT DYES FREE OF AGGREGATION AND SERUM BINDING

[75] Inventors: Walter Beach Dandliker, La Jolla; Mao-Lin Hsu, Fountain Valley, both of Calif.

[73] Assignee: Hyperion, Inc., Miami, Fla.

[21] Appl. No.: 08/865,812

[22] Filed: May 30, 1997

Related U.S. Application Data

[63] Continuation-in-part of application No. 08/476,544, Jun. 7, 1995, which is a continuation-in-part of application No. 08/346,098, Nov. 29, 1994, Pat. No. 5,677,199, which is a division of application No. 07/701,449, May 15, 1991, Pat. No. 5,403,928, which is a continuation-in-part of application No. 07/523,601, May 15, 1990, abandoned, said application No. 08/476,544, and a continuation-in-part of application No. 08/333,603, Nov. 2, 1994, Pat. No. 5,641,878, which is a continuation of application No. 07/701,465, May 15, 1991, abandoned, which is a continuation-in-part of application No. 07/524,212, May 15, 1990, abandoned.

[51] Int. Cl.⁶ ............ C07D 487/22; C09B 47/04; C07F 7/08; G01N 33/53
[52] U.S. Cl. ............ 540/145; 540/472; 540/474; 436/501; 436/800; 436/536; 436/518
[58] Field of Search ............ 540/122, 145, 540/128, 472, 474; 436/501, 800, 536, 518

[56] References Cited

U.S. PATENT DOCUMENTS

| | | | |
|---|---|---|---|
| 2,951,797 | 9/1960 | Sharp et al. | 204/158 |
| 3,116,256 | 12/1963 | D'Alelio et al. | 524/88 |
| 3,287,470 | 11/1966 | Pugin et al. | 106/410 |
| 4,104,466 | 8/1978 | Tsuchida et al. | 540/145 |
| 4,404,366 | 9/1983 | Boguslaski et al. | 536/18.1 |
| 4,614,723 | 9/1986 | Schmidt et al. | 436/536 |
| 4,707,454 | 11/1987 | Hendrix | 436/546 |
| 4,732,570 | 3/1988 | Baumgartner et al. | 524/88 |
| 4,822,733 | 4/1989 | Morrison et al. | 435/6 |
| 4,822,877 | 4/1989 | Inada et al. | 540/145 |
| 4,849,207 | 7/1989 | Sakata et al. | 424/1.1 |
| 4,877,872 | 10/1989 | Morgan et al. | 540/145 |
| 4,886,744 | 12/1989 | Arnost et al. | 435/6 |
| 5,053,423 | 10/1991 | Liu | 514/410 |
| 5,059,510 | 10/1991 | Jones et al. | 540/121 |
| 5,135,717 | 8/1992 | Renzoni et al. | 422/61 |
| 5,177,200 | 1/1993 | Kluger et al. | 524/88 |
| 5,378,634 | 1/1995 | Shigetoh et al. | 436/91 |
| 5,403,928 | 4/1995 | Arrhenuis | 540/128 |
| 5,593,867 | 1/1997 | Walker et al. | 435/91.2 |

FOREIGN PATENT DOCUMENTS

| | | |
|---|---|---|
| 0260098 | 3/1988 | European Pat. Off. |
| 0336879 | 10/1989 | European Pat. Off. |
| 0502723 | 9/1992 | European Pat. Off. |
| 0597389 | 5/1994 | European Pat. Off. |
| 0609894 | 8/1994 | European Pat. Off. |
| 63-215689 | 3/1987 | Japan . |
| 63-264674 | 4/1987 | Japan . |
| 62-249986 | 10/1987 | Japan . |
| 9002747 | 3/1990 | WIPO . |
| 9118006 | 11/1991 | WIPO . |
| 9118007 | 11/1991 | WIPO . |
| 9319366 | 9/1993 | WIPO . |

OTHER PUBLICATIONS

Barrett et al., "Phthalocyanines and Related Coumpounds. Part XV. Tetrabenztriazaporphin: its Preparation from Phthalonitrile and a Proof of its Structure," *Phthalocyanines and Related Coumpounds—Part XV*, pp. 1809–1820 (1939).

Castillo, "Bis (Metilsiloxi) Ftalocianinas Silicio (IV)," *Rev. Latinoamer. Quim.* 10:113–116 (1979).

Devlin et al., "Homogeneous Detection of Nucleic Acids by Transient–State Polarized Fluorescence," *Clin. Chem.* 39/9:1939–1943 (1993).

Diamandis, "Automation of Molecular Diagnositics," *Clinical Chemistry* 42(1):7–8 (1996).

Grant et al. (eds), *Grant & Hackh's Chemical Dictionary*, 5th edition, McGraw–Hill Book Company, p. 241.

Hanack et al., "Synthesis and Properties of a New Kind of One–Dimensional Conductor. VIII. Synthesis and Characterization of trans–BIS–1–Alkynyl Substituted Silicon, Germanium, Tin Phthalocyanines and Germanium Hemiporphyrazines," *Journal of Organometallic Chemistry* 204:315–325 (1981).

Hartmann et al., "Polymere mit dem Zentralatom eines Macrocyclus inder Hauptkette, 2: Polykondensations–reaktionen mith Germaniumkomplexen des Phthalocyanin und meso–Tetraphenyloporphins," *Die Makromolekulare Chemie* 176:831–847 (1975).

Hartmann et al., "Polymers with the Central Atom of a Macrocycle in the Main Chain 2. Polycondensation Reactions with Germanium Complexes of Phthalocyanine and Meso–Tetra–Phenylporphin," *Chemical Abstracts* 83:4 at abstract no. 79670p (1975).

Joyner and Kenney, "Phthalocyaninosilicon Compounds," *Inorganic Chemistry* 1:236–238 (1962).

Kricka, "Ch. 2—Labeling," in *Ligand–Binder Assays: Labels and Analytical Strategies*, Marcel Dekker, Inc., New York pp. 15–51 (1985).

Leznoff and Lever editors, *Phthalocyanines: Properties and Applications* vol. 2, pp. 29–37 and 168–170 (1993).

Leznoff and McKeown, "Preparation of Substituted Tetrabenzotriazaporphyrins and a Tetranaphthotriazaporphyrin: A Route to Mono–meso–substituted Phthalocyanine Analogues," J. Org. Chem. 55:2186–2190 (1990).

Mashiko and Dolphin, "Ch. 21.1—Porphyrins, Hydroporphyrins, Azaporphyrins, Phthalocyanines, Corroles, Corrins and Related Macrocycles," in *Multidenate Macrocyclic Ligands*, pp. 813–898.

(List continued on next page.)

*Primary Examiner*—Richard L. Raymond
*Assistant Examiner*—Pavanaram K. Sripada
*Attorney, Agent, or Firm*—Lyon & Lyon LLP

[57] ABSTRACT

Fluorescent dyes which are free of aggregation and serum binding are provided. These dyes are suitable for applications such as fluorescence immunoassays, in vivo imaging and in vivo tumor therapy.

31 Claims, 10 Drawing Sheets

OTHER PUBLICATIONS

Merck Index (Rahway, J.J., Merck & Co., 1989) p. 172.

Meyer et al., "Polymere mit dem Zentralatom eines Makrocyclus in der Hauptkette; 4. Kovalenter Einbau von Aluminium–, Silicium–and Germaniumkomplexen des Phthalocyanins in Polester," *Die Angewandte Macromolekulare Chemie* 72:173–184 (1978).

Meyer et al., "Polymers with the Central Atom of a Macrocycle in the Main Chain. 1. Polycondensation reactions with phthalocyaninato silicon and hemiporphyrazinato germanium compounds," *Chemical Abstracts* 81:2 at abstract no. 152673g (1974).

Meyer et al., "Polymers with the Central Atom of a Macrocycle in the Main Chain. 4. Covalent Incorporation of Aluminum, Silicon, and Germanium Complexes of Phthalocyanine in Polyesters," *Chemical Abstracts* 90(14):1 at abstract no. 104387f (1979).

Moser and Thomas, *Phthalocyanine Compounds*, Reinhold Publishing Company, New York (1963) (Table of Contents Only).

Moser and Thomas (editors), *The Phthalocyanines*, CRC Press, Inc., Boca Raton, FL, vol. 1:123–127.

Seckinger, "Strand Displacement Amplification and Fluoresence Polarization," *Clincal Chemistry* 42(10):1720 (1996).

Sielcken et al., "Phthaloocyaninato Polysiloxanes Substituted with Crown Ether Moieties," *J. Amer. Chem. Soc.* 112(8):3086–3093 (1990).

Walker et al., "Strand Displacement amplification (SDA) and transient–state fluorescence polarization detection of *Mycobacterium tuberculosis* DNA," *Clinical Chemistry* 42(1):9–13 (1996).

Wilkinson et al. (editors), *Comprehensive Coordination Chemistry: The Synthesis, Reactions, Properties & Applications of Coordination Compounds vol. 2—Ligands*, Pergamon Press, pp. 859–870 (1987).

Meyer et al., Angew Makromol. Chemie 72 (1978) pp. 173–184.

FLUORESCENT DYES FREE OF AGGREGATION AND SERUM BINDING

RELATED APPLICATIONS

This application is a continuation-in-part application of U.S. patent application Ser. No. 08/476,544, filed Jun. 7, 1995, which is (a) a continuation-in-part of U.S. patent application Ser. No. 08/346,098, filed Nov. 29, 1994, now U.S. Pat. No. 5,677,199, which is a divisional of U.S. patent application Ser. No. 07/701,449, filed May 15, 1991, (now U.S. Pat. No. 5,403,928) which was continuation-in-part of U.S. patent application Ser. No. 07/523,601, filed May 15, 1990, now abandoned; and (b) a continuation-in-part application of U.S. patent application Ser. No. 08/333,603, filed Nov. 2, 1994, now U.S. Pat. No. 5,641,878, which is a continuation of U.S. patent application Ser. No. 07/701,465, filed May 15, 1991, now abandoned, which was a continuation-in-part of U.S. patent application Ser. No. 07/524,212, filed May 15, 1990, now abandoned.

All of the above applications are incorporated herein by reference in their entirety including any drawings.

FIELD OF THE INVENTION

The present invention is directed to fluorescent dyes useful as marker components for use in fluorescent probes for binding assays such as immunoassays, hybridization assays, receptor assays, etc., also for in vivo imaging and in vivo tumor therapy.

BACKGROUND OF THE INVENTION

Publications and other reference materials referred to herein are incorporated herein by reference and are numerically referenced in the following text and respectively grouped in the appended Bibliography which immediately precedes the claims.

The following description of the background of the invention is provided to aid in the understanding of the invention and is not admitted to describe or constitute prior art to the claimed invention.

The detection of small quantities of a substance may be accomplished using detectably labeled marker components. Fluorescent dyes may be used as labels in such marker components. Fluorescent dyes having greater sensitivity of fluorescent measurement are needed in order to measure substances or phenomena at lower and lower concentrations with accuracy. In fluorescence assays, the sensitivity of measurement is usually limited by the ratio of the signal obtained from a fluorescent label divided by the background signal. Accordingly, in order to provide fluorescent labels having high sensitivity one needs to minimize the magnitude of the background signal obtained and to maximize the signal from the fluorescent label.

Fluorescence assays are often used to measure substances which occur in biological materials. Such biological materials, such as serum or a cellular extract, contain a variety of components which exhibit fluorescence and may give appreciable background or ambient fluorescence which may interfere with measurement of the signal from the fluorescent label.

One way to decrease the interference from background fluorescence is to use as fluorescent labels dyes having longer emission wavelengths than the substances in a sample which give rise to background fluorescence. Most substances which constitute background autofluorescence in biological materials emit in the range of about 300 to about 650 nm. For example, in human serum at a wavelength of about 725 nm background fluorescence is below the detection levels of conventionally used equipment. Fluorescent dyes having emission wavelengths which reduce interference from background fluorescence include cyanines, porphyrins and azaporphyrins. However, it has been found that the use of such labels in fluorescence assays is limited by the problems of solvent sensitivity (significantly decreased fluorescence intensity in the aqueous assay solution in comparison to dimethylformamide) and non-specific binding to biological materials.

Other properties which affect sensitivity include the magnitude of the extinction coefficient and quantum yield of the fluorescent label and its decay time. Fluorophores have a characteristic fluorescence (or "natural") lifetime, that is, the time period over which the fluorescence intensity decreases to about 37% (l/e) of its initial value in the absence of any deactivating factors. The decay time is the time period over which the decrease to the 37% (l/e) level of fluorescence is actually observed in realistic situations. Decay time may be affected by external factors, thus, a fluorophore which has a long natural lifetime may have a short observed decay time. A shortened decay time indicates deactivation of the excited state of the fluorophore and a resultingly decreased quantum yield (fluorescence quanta emitted per quantum absorbed), resulting in a smaller observed signal than is potentially there (the fluorophore loses energy as heat rather than by fluorescence emission).

Use of fluorophores having long decay times is especially important in techniques such as transient state assays where there is a need for fluorophores whose emissions may be measured over a time period of about 10 to about 20 nanoseconds. Accordingly, there is a need for fluorophores which do not suffer deactivation over such a time period.

It has been found that for fluorophores natural lifetime and extinction coefficient vary antibactically. Also, fluorophores having longer fluorescent lifetimes are more apt to be deactivated. Accordingly, fluorophores having enhanced decay times, i.e. having decay times which approach their natural lifetime, offer greater quantum yields and, thus, greater sensitivity.

SUMMARY OF THE INVENTION

The present invention relates to marker components which are useful as detectable labels. These marker components may be used as detectable labels in diagnostic reagents and are particularly useful in assays such as fluorescence binding assays and other immunoassays. According to the present invention, detectably labeled marker components are provided that comprise a fluorophore moiety coupled to two solubilizing polyoxyhydrocarbyl moieties which in the presence of serum components in aqueous solutions are characterized by transient state fluorescence emission having parallel and perpendicular components of substantially the same intensities as without serum.

The present invention is directed to a detectably labeled marker component which comprises a fluorophore moiety comprising a luminescent substantially planar molecular structure coupled to two solubilizing polyoxyhydrocarbyl moieties, one located on either side of the planar molecular structure. Such molecular components are also believed to be useful in methods such as those described in Walker, et al, *Clinical Chemistry* 42:1 (1996); *Clinical Chemistry* 39:9 (1993); U.S. Pat. No. 5,593,867; and, European Patent Application 93117909.7, which are incorporated herein by reference or in their entirety including any drawings.

In one aspect, the present invention is directed to detectably labeled marker components which comprise a fluorophore moiety which comprises a substantially planar macrocyclic multidentate ligand coordinated to a central atom and two solubilizing polyoxyhydrocarbyl moieties, one linked on either side of the plane of the multidentate ligand to the central atom.

In one preferred aspect, the present invention is directed to a marker component comprising a fluorophore moiety which comprises a substantially planar multidentate macrocyclic ligand coordinated to a central atom capable of coordinating with two axial ligands which are coordinated to the central atom on either side of the macrocyclic ligand.

The commonly assigned U.S. patent application of Peter Arrhenius "Fluorescent Marker Components and Fluorescent Probes" Ser. No. 07/524,212 discloses marker components which comprise a fluorophore moiety linked to at least one solubilizing polyoxyhydrocarbyl moiety which have decreased solvent sensitivity and diminished binding to human serum albumin ("HSA"). Although the marker components disclosed exhibited surprisingly advantageous properties, when used with samples having human serum, some exhibited non-specific binding to a serum component which was not HSA. Additionally, some marker components exhibited a low level of solvent sensitivity indicating some residual quenching and aggregation. Some of those marker components did not migrate on gels and on TLC and when chromatographed on a molecular sizing gel filtration column eluted, with the void volume, (molecular weight 40,000) indicating some apparent aggregation.

Surprisingly, it has been found that marker components of the present invention which comprise a macrocyclic multidentate ligand having two solubilizing polyoxyhydrocarbyl moieties one located on either side of the plane of the multidentate ligand exhibit no detectable non-specific binding to serum components, and exhibit no detectable solvent sensitivity. These marker components also exhibit enhanced decay times which approach their natural (fluorescent) lifetimes.

The marker components of the present invention are particularly suitable as detectable labels for use in assays for detecting analyte in aqueous solution. These marker components are useful as fluorescent labels for incorporation in fluorescent probes. Some of these marker components are useful as phosphorescent labels. The components of the present invention are also useful as labels for agents for in vivo imaging and also as labels for agents used in in vivo tumor therapy.

Accordingly, in general, preferred are fluorophores which efficiently produce fluorescence upon excitation with light whose wavelength falls in the range of about 200 to about 1000 nanometers, preferably in the range of about 600 to 800 nanometers.

Suitable fluorophores include those which absorb and/or emit at wavelengths which are distinguishable from the excitation and emission maxima of other solution components (such as proteins present in a sample) to minimize background fluorescence.

Since these marker components are particularly useful in assays using samples of biological fluids, for those uses, preferred are fluorophores having excitation and/or emission wavelengths of at least about 500 nanometers which reduces interference from the ambient fluorescence of other sample components. Some samples, such as serum, may exhibit considerable interfering background fluorescence from flavins, flavoproteins, NADH, etc. when excitation wavelengths less than 500 nm are used.

For certain applications, such as fluorescence polarization immunoassays, preferred fluorophores may also exhibit a high degree of fluorescence polarization when in the bound form, preferably greater than about 10% of the theoretical maximum value for an observable polarization. For certain applications such as fluorescence transient state assays, preferred fluorophores are also characterized by measured fluorescence decay times in the range of about 1 nanosecond to about 50 nanoseconds, preferably in the range of about 5 to about 20 nanoseconds. For other applications, such as phosphorescent labels, fluorophores having even longer decay times may be used.

Thus, preferred are fluorophores which produce fluorescent light efficiently, i.e., which are characterized by high absorbitivity at the appropriate wavelength and high fluorescence quantum yields. For certain applications, preferred fluorophores have measured fluorescence decay times on the order of at least 2 nanoseconds and exhibit a high degree of fluorescence polarization.

Preferred solubilizing polyoxyhydrocarbyl moieties include water soluble carbohydrates such as glucose, sucrose, maltotriose, and the like; water soluble carbohydrate derivatives such as gluconic acid and mannitol and oligosaccharides; and water soluble polymers such as polyvinylpyrrolidone, poly(vinylalcohol), poly(ethylenimine), polyacrylic acid, polyacrylamide, ethylene oxide copolymers such as Pluronic (a propylene oxide copolymer, available from BASF) and Tetronic (BASF) polyol surfactants; and polyethers, including water soluble polyoxyalkylene polymers, particularly poly(ethylene glycol) ("PEG") and poly(ethylene glycol) derivatives such as polytethylene glycol) methyl ether, poly(ethylene glycol) silicon derived ethers and the like.

In one aspect, the present invention is directed to marker components comprising a fluorophore moiety which comprises a substantially planar, multidentate macrocyclic ligand coordinated to a central atom capable of coordinating with two axial ligands and two polyoxyhydrocarbyl moieties which are attached as axial ligands to the central atom. For use as marker components in fluorescence binding assays, suitable central atoms are those to which may coordinate two axial ligands and which are not of high enough atomic number to cause extensive fluorescence quenching by transition to the triplet state. Preferred elements for the central atom include silicon, germanium, phosphorus, and tin, especially preferred are silicon and germanium.

These marker components may be used as labels for labeling an analyte, antigen, antibody, nucleic acid or other molecule. These marker components may be optionally functionalized so as to include a linker arm which allows the marker component to be linked to the analyte, antigen, antibody or other molecule. A variety of linker arms which are suited to this purpose have been described. (Ref. 1). The marker component is linked to the analyte, antigen, antibody or other molecule using conventional techniques.

DEFINITIONS

As used herein, the following terms have the following meanings unless expressly stated to the contrary:

The term "analyte" refers to the compound or compound to be measured in an assay which may be any compound for which a receptor naturally exists or can be prepared which is mono- or polyepitopic, antigenic or haptenic, a single or plurality of compounds which share at least one common epitopic site or a receptor.

The term "axial ligand" refers to a substituent which, together with a macrocyclic ligand, forms a coordination complex with a central atom. The axial ligand lies normal to the plane described by the macrocyclic ligand.

The term "fluorescent probe" refers to a marker component comprising a fluorophore moiety which is bonded to or coordinates either directly or via a linker arm to an analyte, antigen, hapten, antibody or other molecule which is used in an assay, such as a fluoroimmunoassay to determine the presence of and/or quantitate a substance of interest.

The term "solvent sensitivity" refers to changes in the fluorescence behavior of a molecule depending on the solvent system in use, most notably referring to differences in fluorescence behavior in aqueous solution in comparison with organic solvents (such as DMF). Many fluorophores which exhibit high fluorescence intensity in organic solvents such as DMF show substantially decreased fluorescence intensity in aqueous solution.

Fluorescence intensity is related to sample concentration and the intensity of the exciting radiation. The fluorescence intensity of a particular dye can be correlated to its characteristic light absorptivity (extinction coefficient) and fluorescence quantum efficiency, as well as environmental factors.

The term "specific binding pair" refers to two different molecules (or compositions) wherein one of the molecules has an area on the surface or in a cavity which specifically recognizes and binds to a particular spatial and polar organization of the other molecule or molecular complex involving other molecules.

The term "binding partner" refers to a molecule or molecular complex which is capable or specifically recognizing or being recognized by a particular molecule or molecular complex.

The term "bound" refers to the condition in which a binding interaction has been formed between a molecule and its specific binding partner.

The term "synbatic" refers to two variables that are related such that when one increases, the other also increases; however, they need not increase at rates that are proportional to each other.

The term "antibatic" refers to two variables that are related such that when one increases, the other decreases; however they need not change at rates inversely proportional to each other.

The term "decay time" is the time which must elapse in order for the concentration of excited molecules to decrease from its initial concentration to 1/e of that value.

The summary of the invention described above is non-limiting and other features and advantages of the invention will be apparent from the following description of the preferred embodiments, and from the claims.

DETAILED DESCRIPTION OF THE INVENTION

I. PREFERRED MARKER COMPONENTS

A. Preferred Fluorophore Moieties

Figure 1A:
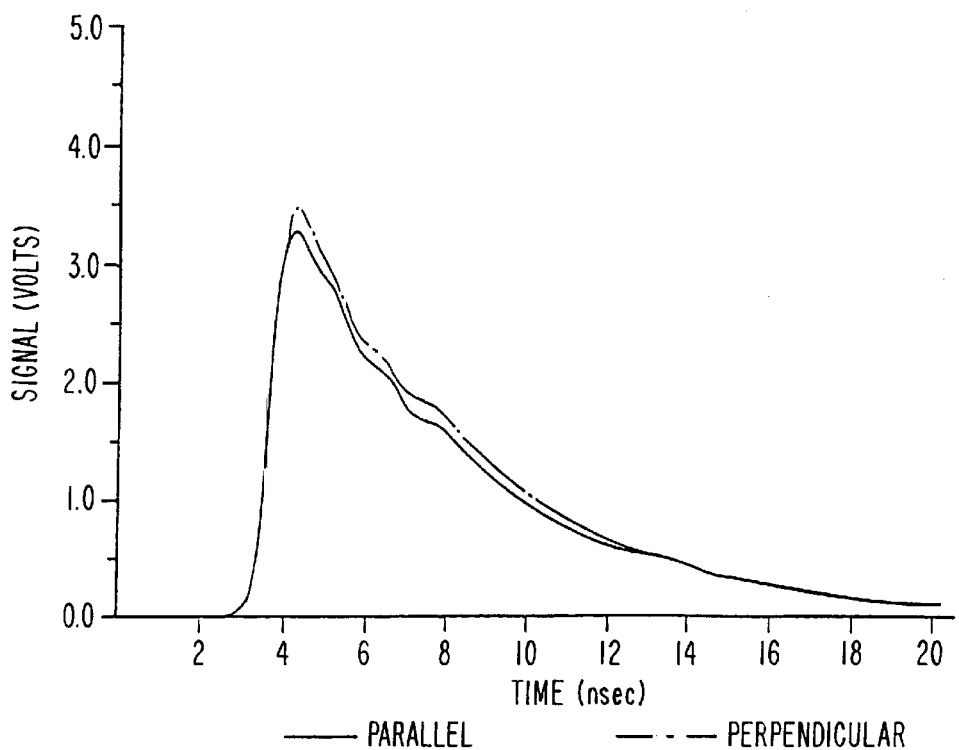
FIGS. 1A, 1B and 1C depict transient state fluorescence emission for a marker component prepared according to Example 3.

Suitable fluorophore moieties comprise a luminescent substantially planar molecular structure. Preferred are fluorophore moieties in which the luminescent substantially planar molecular structure comprises a substantially planar macrocyclic multidentate ligand which coordinates a central atom which may coordinate with two axial ligands, one on either side of the macrocyclic ligand (i.e. having a trans orientation).

Preferred central atoms are elements which may form octahedral coordination complexes containing two ligands with a trans or axial orientation, on either side and perpendicular to the planar macrocyclic ligand. For use as fluorescent marker components in certain applications the central atom should not have too high atomic number (about 30 or less) so that fluorescence is largely lost by transition to the triplet state. For uses such as in vivo tumor therapy, higher atomic weight atoms may be used, or in separation-type assays or for phosphorescent labels.

Preferred multidentate ligands include nitrogen-containing macrocycles which have conjugated ring systems with pi-electrons. These macrocycles may be optionally substituted, including substitution on bridging carbons or on nitrogens. Suitable macrocycles include derivatives of porphyrins, azaporphyrins, corrins, sapphyrins and porphycenes and other like macrocycles having conjugated π-electron ring systems. In view of the fact that they incorporate many of the above-noted characteristics, an especially preferred class of macrocycles comprise porphyrin derivatives, and azaporphyrin derivatives (porphyrin derivatives wherein at least one of the bridging carbons is replaced by a nitrogen atom). Azaporphyrin derivatives include derivatives of mono-, di- and triazaporphyrin and porphyrazine. These macrocycles may optionally have fused aromatic rings. These azaporphyrin derivatives include phthalocyanine, benzotriazaporphyrin and naphthalocyanine and their derivatives. The preparation and fluorescent qualities of many of these compounds are known and some are available commercially. (Ref. 2, 3, 4, 5).

For certain applications, such as fluorescence polarization assays, preferred are azaporphyrin derivatives which exhibit a high degree of polarization when bound, that is, those which emit strongly polarized light. For these applications, preferred are macrocycles having lower degrees of symmetry, preferably having lower symmetry than $D_{4h}$. One preferred group includes macrocycles having at least one fused aromatic ring. Thus, preferred macrocycles include azaporphyrin derivatives having fused aromatic rings at positions which result in decreased symmetry. Preferred classes of azaporphyrin derivatives comprise derivatives of monoazaporphyrin, diazaporphyrin, and triazaporphyrin having lower than $D_{4h}$ symmetry.

B. Preferred Solubilizing Polyoxyhydrocarbyl Moieties

Preferred solubilizing polyoxyhydrocarbyl moieties include water soluble carbohydrates such as glucose, sucrose, maltotriose and the like; water soluble carbohydrate derivatives such as gluconic acid and mannitol, and oligosaccharides; polypeptides such as polysine and naturally occurring proteins; and water soluble polymers such as polyvinylpyrrolidone, poly(vinyl alcohol), poly(ethylenimine), polyacrylic acid, polyacrylamide, ethylene oxide copolymers such as Pluronic™ (a polyether) and Tetronic™ (BASF) polyol surfactants and, in particular, polyethers such as other polyoxyalkylenes including poly(ethylene glycol), or other water soluble mixed oxyalkylene polymers, and the like.

A particularly preferred class of solubilizing polyoxyhydrocarbyl moieties comprises poly(ethylene glycol) (PEG) and poly(ethylene glycol) derivatives, such as poly(ethylene glycol) monomethyl ether. Other suitable PEG derivatives include PEG-silicon derived ethers (see Example 9). Many of these polymers are commercially available in a variety of molecular weights. Others may be conveniently prepared from commercially available materials, such as by coupling of an amino-PEG to a haloalkyl silyl or silane moiety. When linked to a fluorophore moiety, these polyoxyhydrocarbyl moieties impart particularly advantageous qualities of solubility in aqueous solution with improved measured fluorescence decay time, and improved fluorescence intensity. Moreover, the resulting marker components are water soluble and show decreased non-specific binding, especially decreased binding to serum albumin which has heretofore been a problem with certain fluorophores, particularly porphyrin or phthalocyanine dyes which have been functionalized with groups such as sulfonate to impart increased water solubility to the molecule. Non-specific binding of fluorophore or marker component impairs the accuracy of the resulting immunoassay. These marker components which comprise fluorophore linked to PEG may also exhibit improved fluorescence intensity in aqueous solution with decreased quenching.

Suitable PEGs may vary in molecular weight from about 200 to about 20,000 or more. Choice of a particular molecular weight may depend on the particular fluorophore chosen and its molecular weight and degree of hydrophobicity, as well as the particular application for which the fluorophore-PEG complex is to be used.

C. Absorbance and Polarization Behavior of Preferred Marker Components

The lack of solvent sensitivity and non-specific binding to HSA and serum components was demonstrated by measurement of absorbance spectra and transient state fluorescence emission.

These marker components which comprise a central atom (for example, silicon) coupled to two PEG moieties may be sensitively characterized by measurements of transient state fluorescence. In such measurements the intensity of the two components polarized either parallel or perpendicular to the direction of polarization of the exciting pulse is monitored over a time period equal to about 3 times the decay time of the marker component. Such curves reflect extinction coefficient, quantum yield, decay time and state of polarization and supply sensitive indications on the chemical and physical condition of the marker component.

For example, if the excited state is being deactivated or converted to the triplet state the overall intensities are lowered and the decay times shortened. If the rotary brownian motion of the molecule is being altered by an increase in viscosity or by being bound to a large molecule, the ratio of the intensity of the parallel to the perpendicular component is increased.

Some marker components according to the present invention show, within experimental error of about 5%, the same intensities, decay time and polarization in DMF (an organic solvent) as in SAP (saline azide phosphate, an aqueous neutral buffer). To some extent these properties are shared by other marker component preparations. A distinctive and important property of the marker components of the present invention is a insensitivity to (and lack of binding to) the components in serum which is evidenced by a lack of any measured effect of serum on the intensities, decay time or relative magnitudes of the polarized components of the fluorescence. This property is crucial for the marker components to be useful for applications such as assays using biological materials.

Figure 3A:
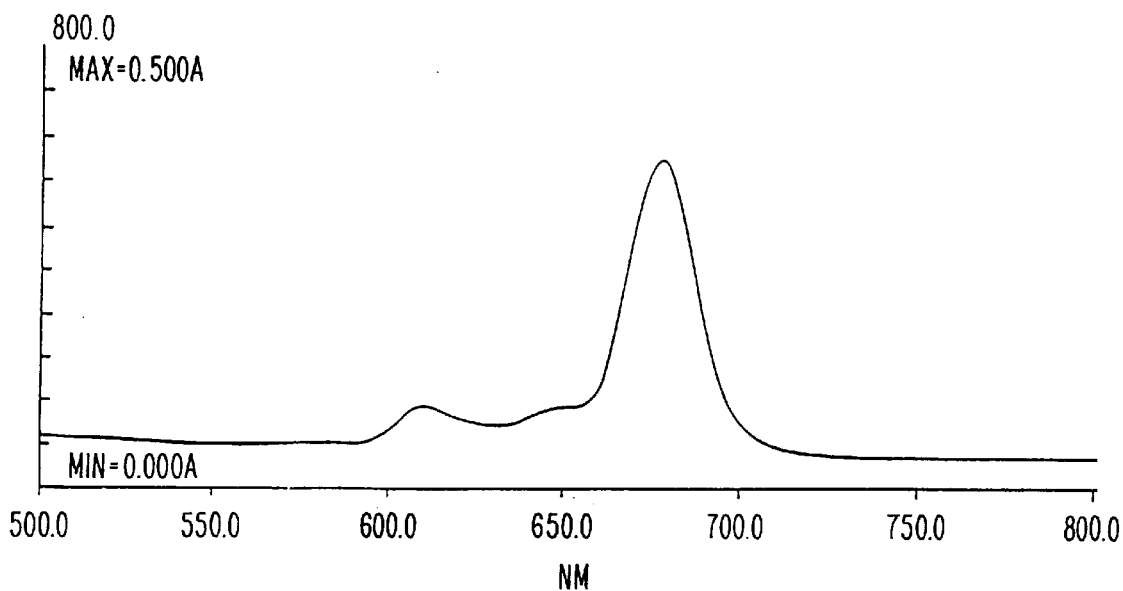
FIGS. 3A and 3B depict visible and near-infrared absorbance of a marker component prepared according to Example 5.
Figure 3B:
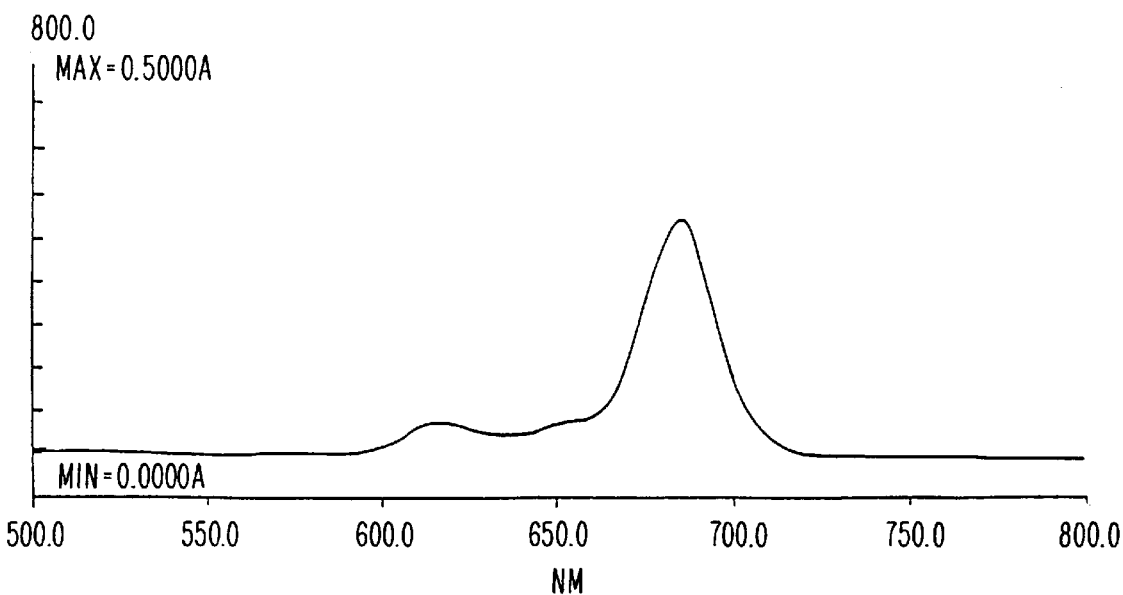

FIGS. 3A and 3B depict the absorbance spectra in the visible and near-infrared range for a product of hydroxy silicon phthalocyanine with PEG monomethyl ether of average molecular weight 350 (see Example 5). These figures show that the positions and heights of the absorbance maxima are nearly identical in DMF, an organic solvent (FIG. 3A), and in SAP (saline azide phosphate), an aqueous buffer solution (FIG. 3B). In contrast, silicon phthalocyanine which is unsubstituted with the solubilizing polyoxyhydrocarbyl axial ligands would be nearly insoluble in either of these solvents and would exhibit only very low absorbance levels in DMF and virtually none in SAP.

Figure 2A:
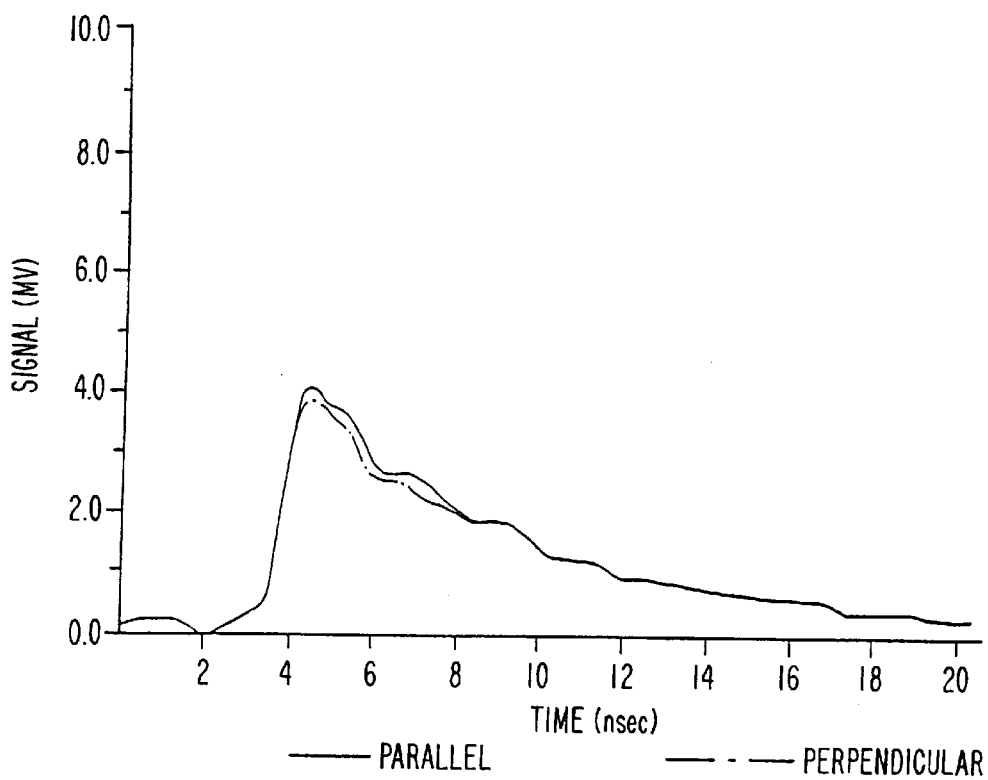
FIGS. 2A and 2B depict transient state fluorescence emission for a marker component prepared according to Example 5.
Figure 2B:
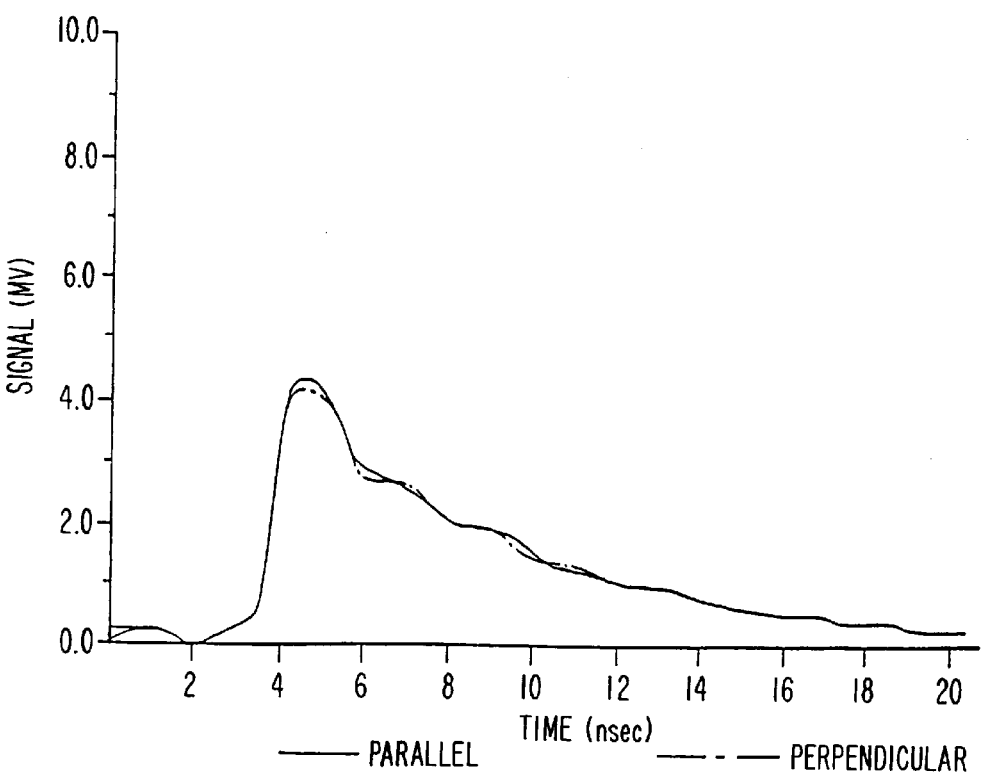

FIGS. 2A and 2B depict transient state fluorescence emission for the same PEG-substituted silicon phthalocyanine as used for FIGS. 3A and 3B. These figures show that emission was virtually unaffected by the addition of human serum (100 $\mu$l) to sample in SAP (3.1 ml total volume). A silicon phthalocyanine solubilized by derivatization of the phthalocyanine macrocycle with sulfonate without the PEG ligands would show changes in both fluorescence intensity and polarization when serum was added. Those changes are abrogated by the replacement of the hydroxy groups with the PEG axial ligands.

Figure 1B:
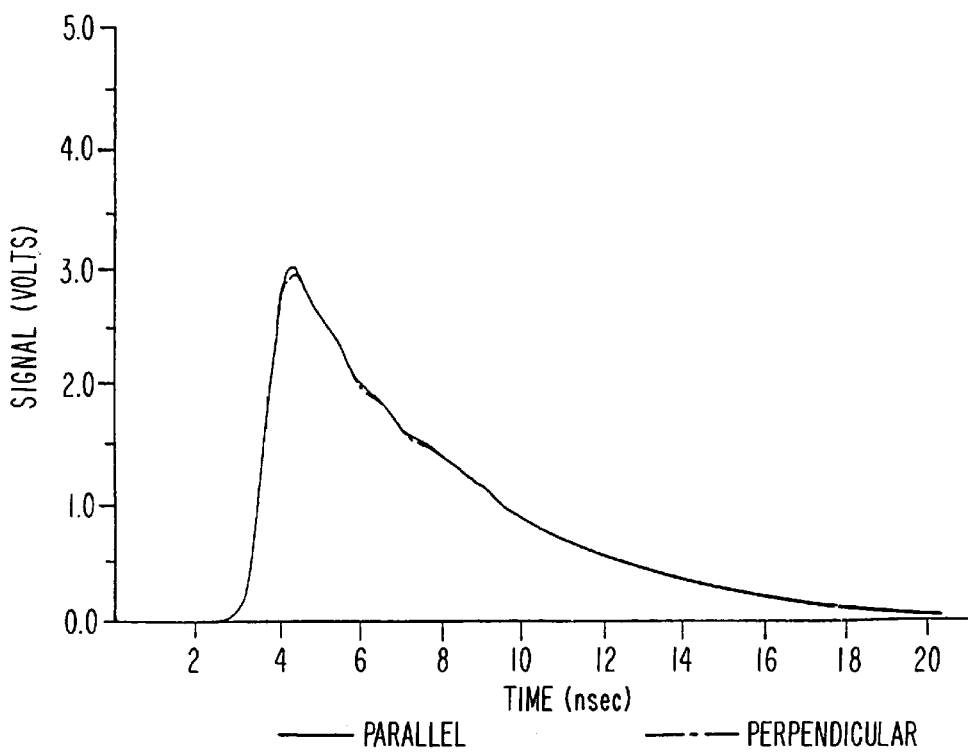
Figure 1C:
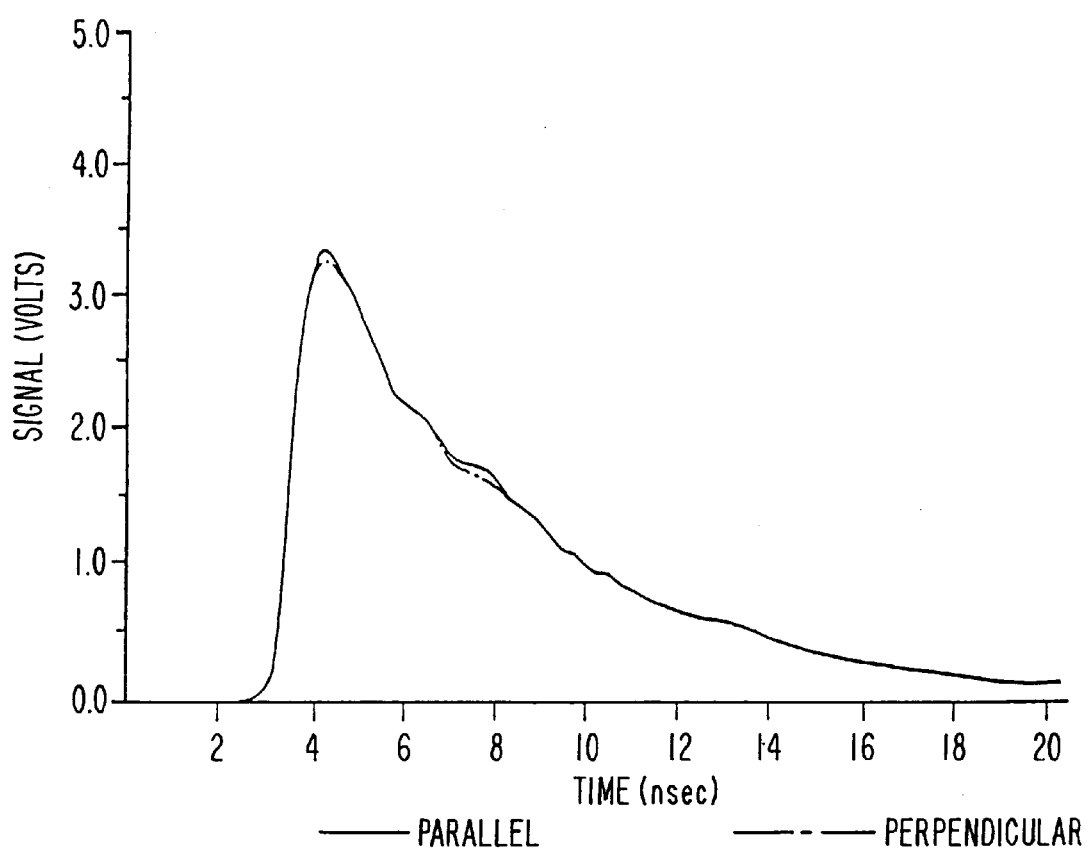

FIGS. 1A, 1B and 1C depict transient state fluorescence emission for a PEG-substituted silicon phthalocyanine where the phthalocyanine macrocycle is sulfonated. This PEG-silicon phthalocyanine derivative demonstrated the same transient state emission in the presence of HSA (100 $\mu$l of 5% HSA FIG. 1B), and HSA plus serum (100 $\mu$l of 5% HSA and 100 $\mu$l serum-FIG. 1C), as it did in buffer alone (SAP-FIG. 1A). These figures demonstrate that sulfonation of the macrocycle did not affect the ability of the axial polyoxyhydrocarbyl solubilizing moieties to prevent non-specific binding of the marker component to either HSA or serum components.

Figure 6A:
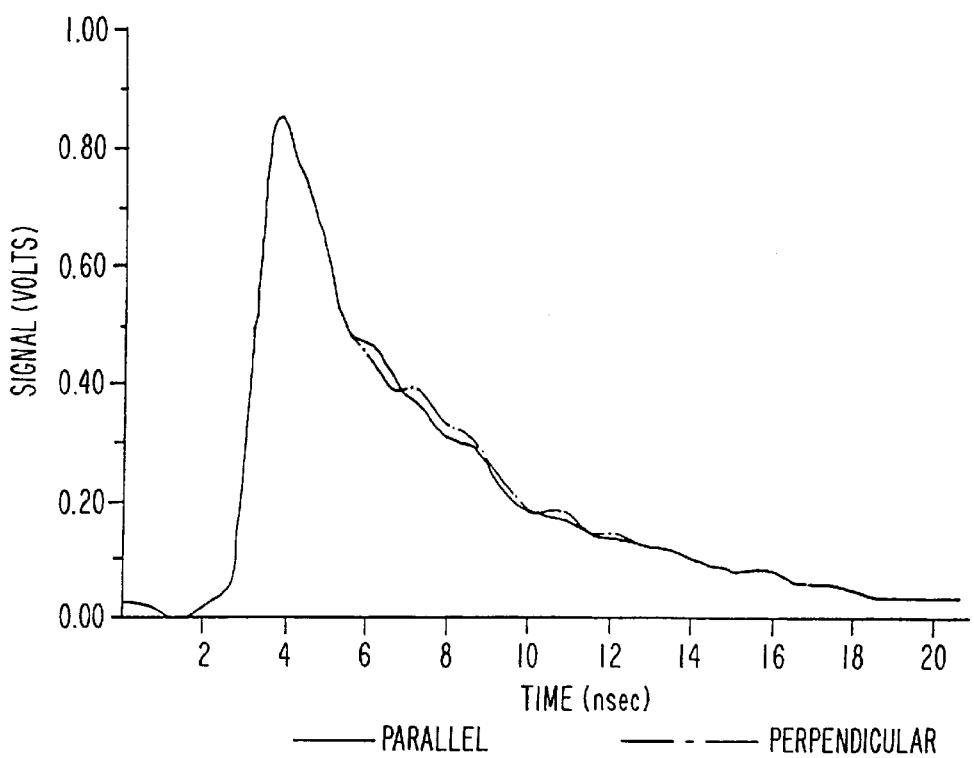
FIGS. 6A, 6B and 6C depict transient state fluorescent emission of sulfonated silicon phthalocyanine prepared according to Example 10.
Figure 6B:
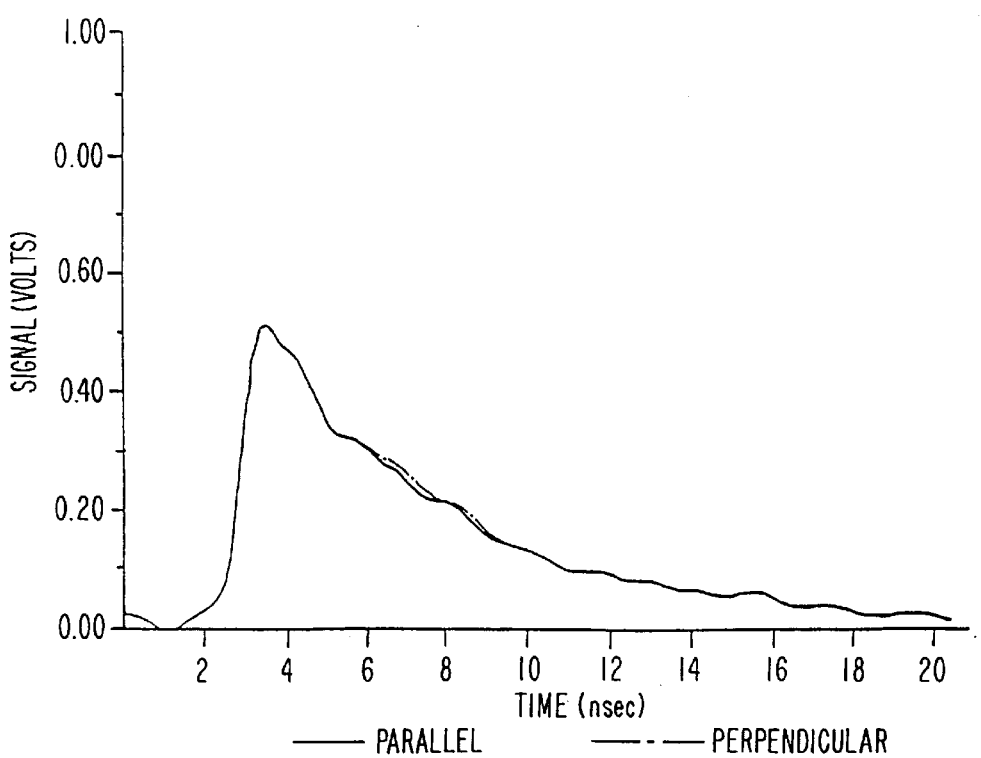
Figure 6C:
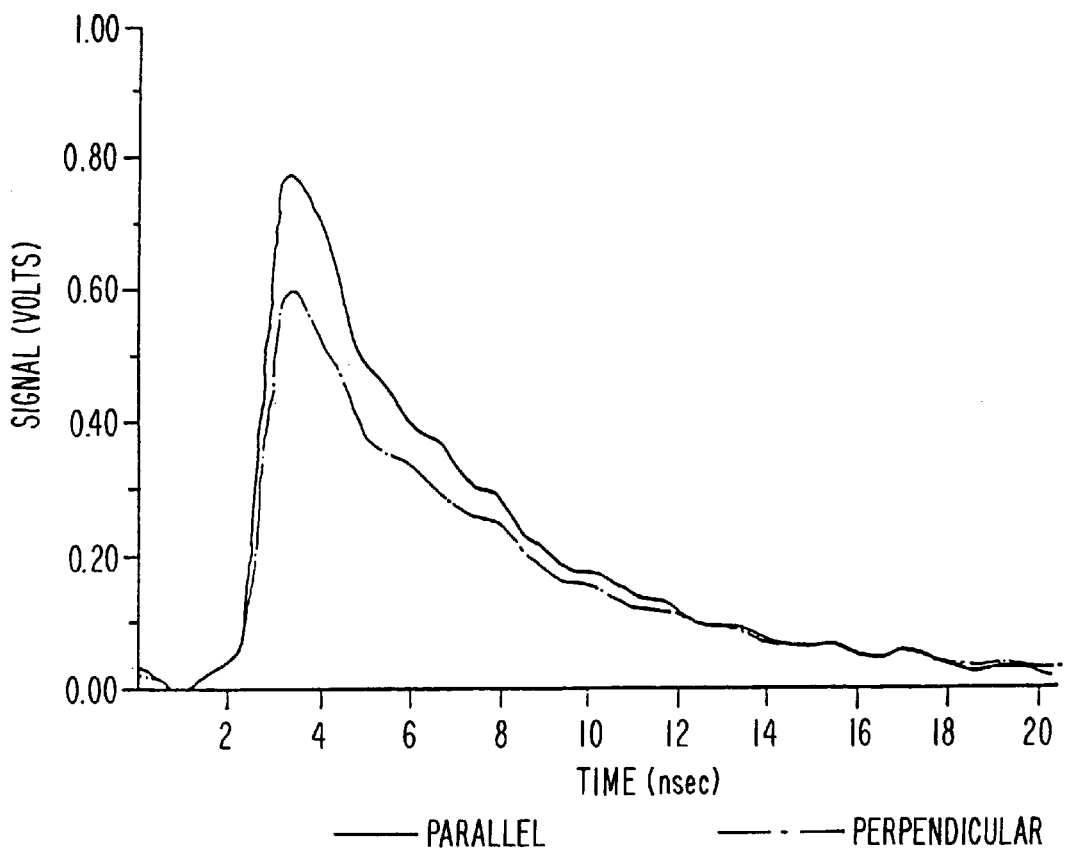

FIGS. 6A, 6B and 6C depict transient state fluorescence emission for a sulfonated silicon phthalocyanine prepared according to Example 10, which does not have any solubilizing polyoxyhydrocarbyl moieties linked to the central silicon atom. FIG. 6A depicts the transient state fluorescence of sulfonated phthalocyanine in DMF which shows the two components polarized either parallel or perpendicular with respect to the polarization of the excitation flash. FIG. 6B depicts the transient state fluorescence of the same material in SAP as FIG. 6A at the same concentration. A comparison of FIGS. 6A and 6B shows that the material is solvent sensitive and that its fluorescence is about 40% quenched in SAP. FIG. 6C depicts the transient state fluorescence of a 3 ml sample of the solution of 6B to which 100 $\mu$l of human serum was added. Comparison of FIGS. 6B and 6C, demonstrates that the addition of serum to the solution produced an enhancement of fluorescence and induced polarization of the emission of this dye such that the parallel and perpendicular components were not of substantially equal intensity. This indicates substantial binding of the sulfonated silicon phthalocyanine to serum components. The change in intensity after addition of the serum is also indicative of binding to serum components.

Figure 7A:
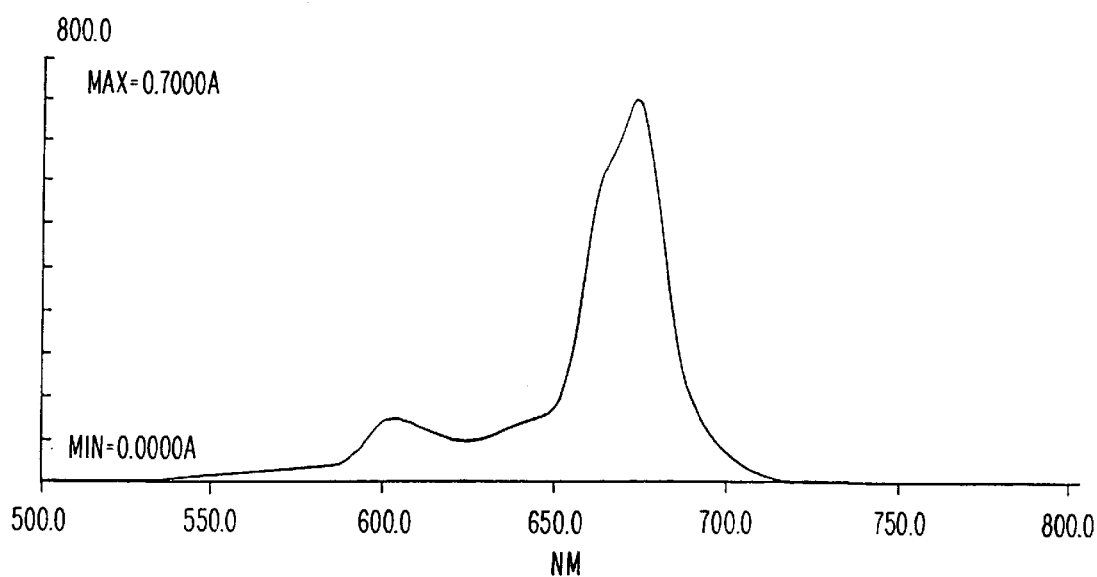
FIGS. 7A and 7B depict visible and near-infrared absorbance of sulfonated silicon phthalocyanine prepared according to Example 10.
Figure 7B:
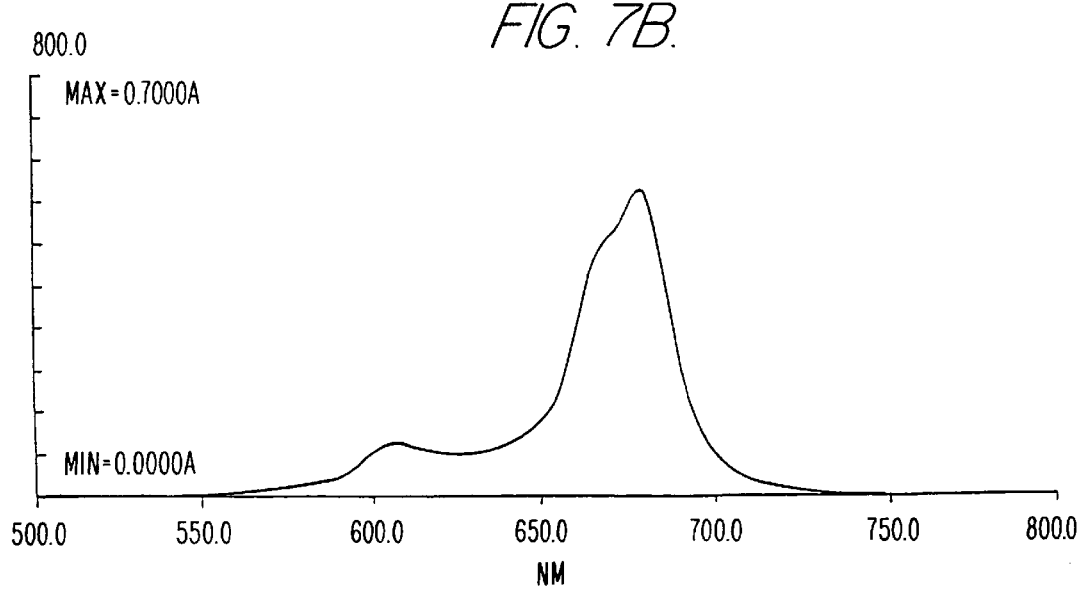
Figure 8:
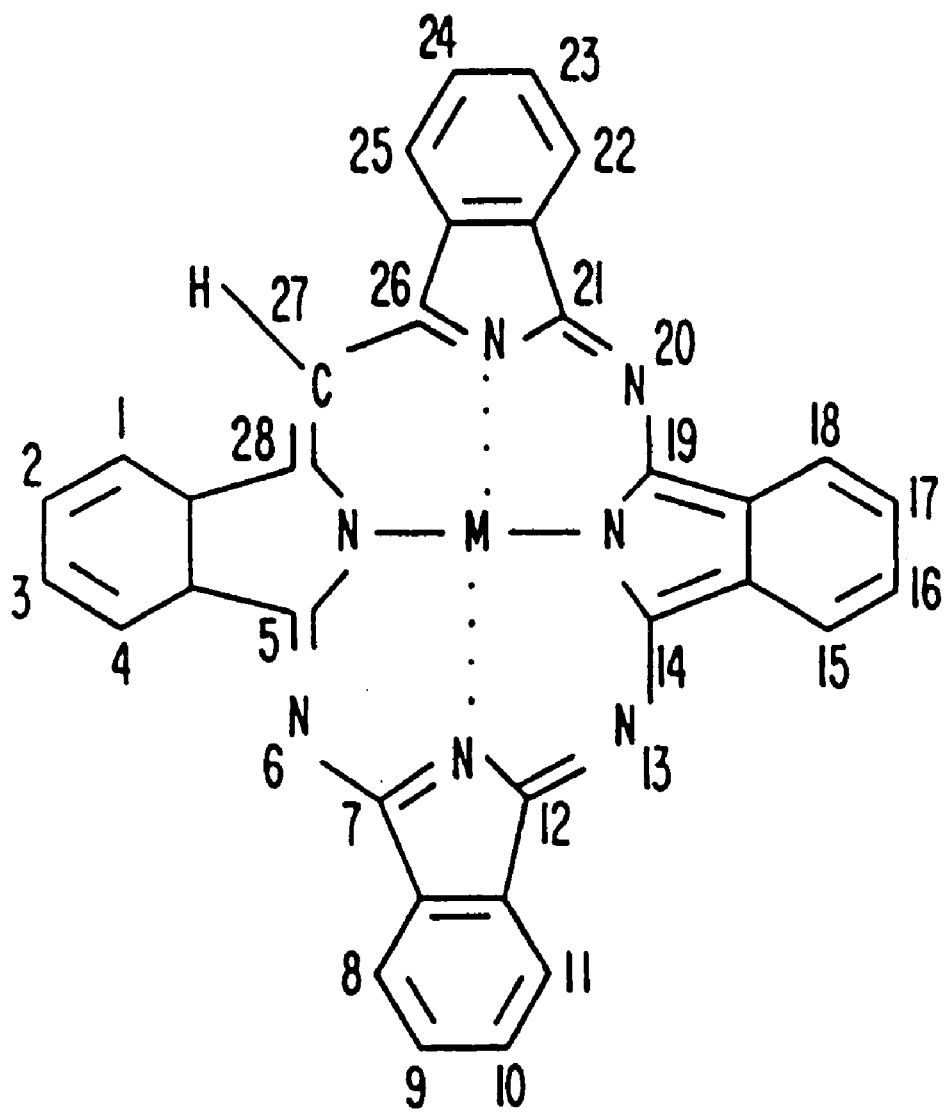
FIG. 8 depicts a tetrabenzotriazaporphyrin moiety with conventional numbering for the macrocyclic ring.

FIGS. 7A and 7B depict visual and near-infrared absorbance of a sulfonated silicon phthalocyanine prepared according to Example 10. FIG. 7A depicts the absorption spectrum of the sulfonated silicon phthalocyanine in DMF. Wavelength maxima and absorbances are 673 nm (0.634) and 603 nm (0.107) respectively. FIG. 7B depicts the absorption spectrum of the sulfonated silicon phthalocyanine in SAP at the same concentration as FIG. 7A. Wavelength maxima and absorbance are 678 nm (0.509) and 606 nm (0.092), respectively.

II. PREPARATION OF PREFERRED MARKER COMPONENTS

According to one method of preparing the preferred marker components of the present invention, the appropriate fluorophore moiety having hydroxy or halide groups as axial ligands is reacted with a reactive form of the solubilizing polyoxyhydrocarbyl moiety in a ligand exchange reaction according to the general reaction scheme:

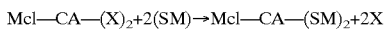

$$Mcl\text{—}CA\text{—}(X)_2 + 2(SM) \rightarrow Mcl\text{—}CA\text{—}(SM)_2 + 2X$$

wherein Mcl denotes the macrocyclic ligand, CA the central atom, X the displaced ligand and SM the solubilizing moiety. This reaction may be carried out neat or, if desired, in solvent. Suitable solvents include quinoline, THF, DMF, imidazole and the like. Suitable reaction temperatures may vary, depending on the nature of the macrocyclic starting material and the solubilizing group. The reaction is generally complete in about 2 minutes to about 24 hours. The reaction mixture can be conveniently heated under reflux or by means such as a sand bath. For convenience, the reaction may be carried out at ambient pressure.

It is believed that this reaction takes place in two steps, with one polyoxyhydrocarbyl group coordinating as an axial ligand at a time.

Figure 4A:
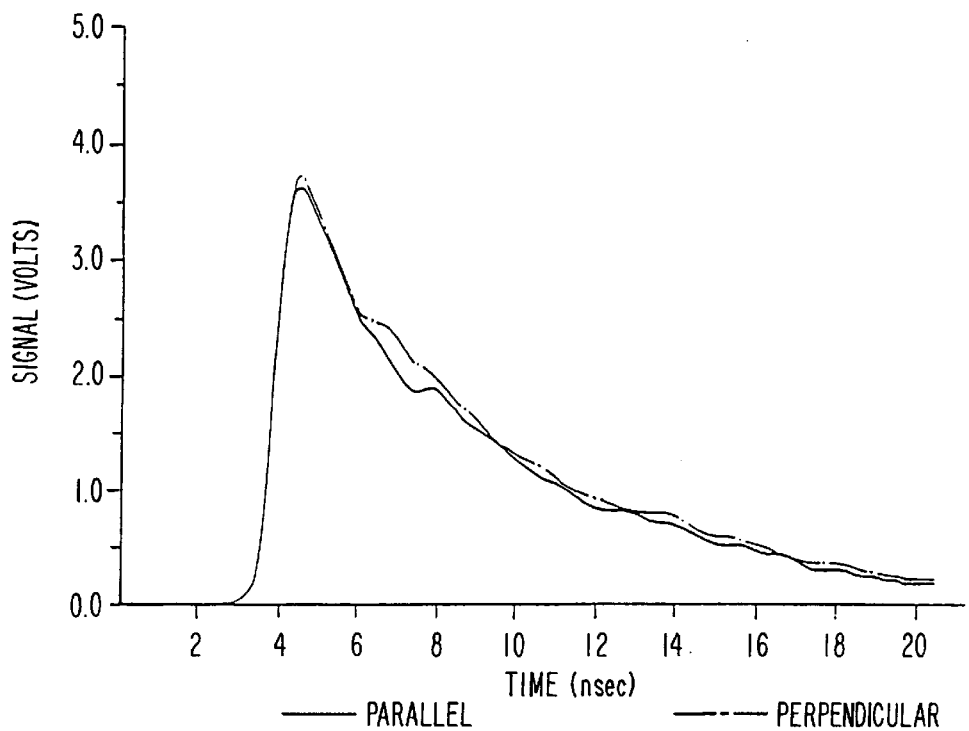
FIGS. 4A and 4B depict transient state fluorescence emission of a product of the first stage ("Early Blue Stage") of the reaction between dihydroxy silicon phthalocyanine and PEG.
Figure 4B:
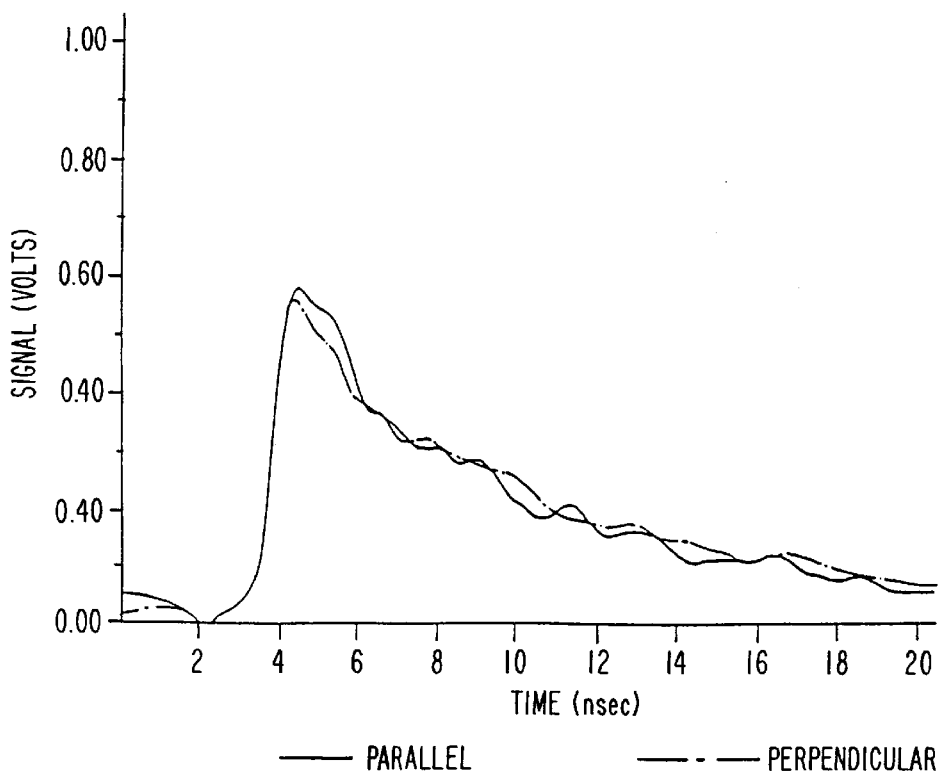
Figure 5A:
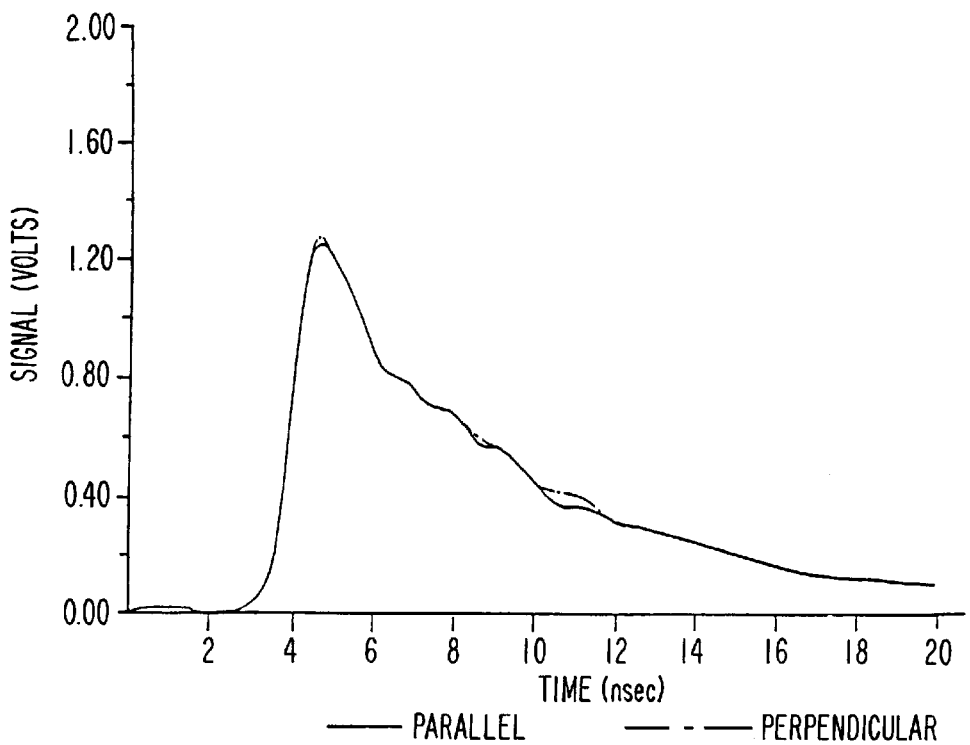
FIGS. 5A and 5B depict the product of the later stage ("Blue Green Product") of the reaction between dihydroxy silicon phthalocyanine and PEG.
Figure 5B:
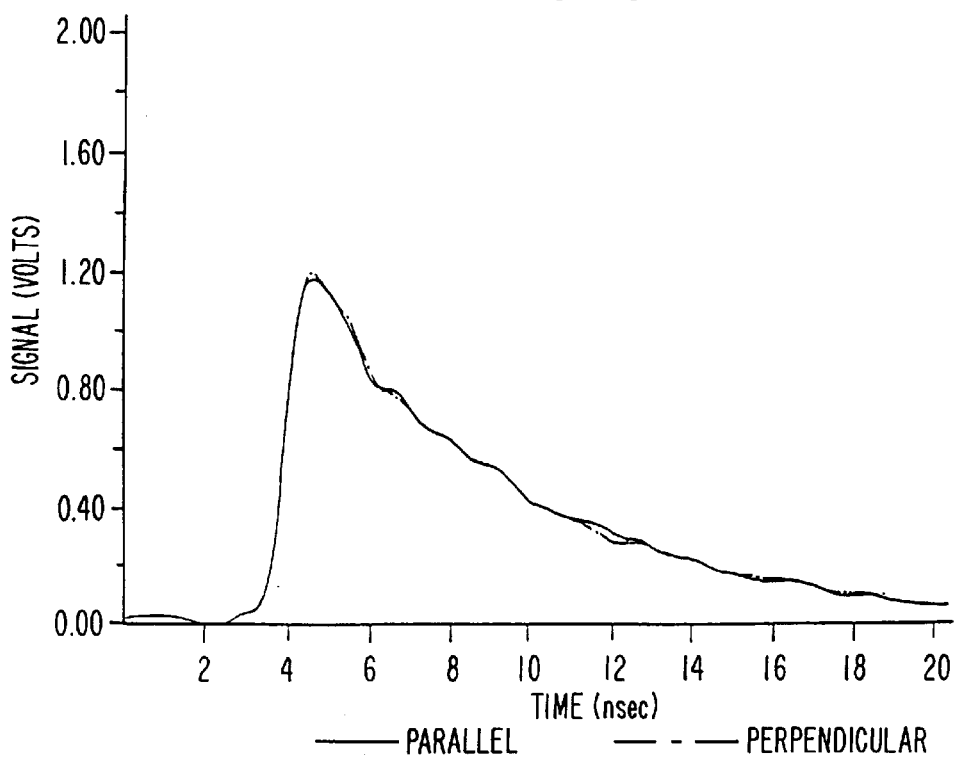

FIGS. 4A, 4B, 5A and 5B demonstrate that the reaction of the polyoxyhydrocarby moiety with the central atom coordinated macrocyclic ligand may proceed in stages. These figures depict products of the reaction of PEG with dihydroxy silicon phthalocyanine (PcSi(OH)$_2$). FIGS. 4A and 4B demonstrate that at the first stage ("Early Blue Stage"), the fluorophore moiety (SiPc), while being rendered soluble in both DMF and SAP (aqueous saline azide phosphate buffer), was markedly sensitive to solvent and was about 85% quenched (note the differences in ordinate scale). FIGS. 5A and 5B demonstrate that product of the latter stage of the reaction ("Blue Green Product"), in contrast, was totally insensitive to solvent and showed the same emission intensity and decay time in either solvent.

III. UTILITY

The marker components of the present invention are useful as fluorescent labels for fluorescent probes and in fluorescence binding assays and also in as labels for in vivo imaging and in vivo tumor therapy.

These marker components may be advantageously used as fluorescent labels in conventional fluorescence binding assays, including fluorescence polarization immunoassays. When so used, these marker components may be linked to one member of a specific binding pair ("labeled binding partner") or an analog of such a member. The marker component may be directly attached or conjugated thereto or attached or conjugated via a linker arm.

These labeled binding partners are useful in assays having a variety of formats, such as assays which involve competition for analyte or analyte binding partner (if a labeled analyte or analyte-analog as used) and may be used in either homogeneous or heterogeneous assays.

In view of their advantageous freedom from aggregation in aqueous solution and lack of solvent sensitivity (indicating no detectable aggregation) in combination with their lack of nonspecific binding to serum components and other biological macromolecules, these markers are especially suited for use in assays for detecting an analyte in a sample containing a biological fluid such as serum. Thus, these marker components may be used as labels for fluorescent probes for detecting analytes in solutions where non-specific binding by serum components would severely compromise sensitivity of an assay, affecting both its accuracy and precision.

Alternatively, these marker components may be used as agents for in vivo imaging. When used as imaging agents, these marker components are conjugated to one member of a specific binding pair to give a labeled binding partner. The labeled binding partner is introduced into an animal. If the other member of the specific binding pair is present, the labeled binding partner will bind thereto and the signal produced by the marker component may be measured and its localization identified.

These marker components may also be used in in vivo tumor therapy. For example, photodynamic therapy involves using the marker component as a photosensitizing agent. The marker component (fluorescent label) is conjugated to a binding partner which may specifically recognize and bind to a component of a tumor cell.

To assist in understanding the present invention, the following examples are included which describe the results of a series of experiments. The following examples relating to this invention should not, of course, be construed in specifically limiting the invention and such variations of the invention, now know or later developed, which would be within the purview of one skilled in the art are considered to fall within the scope of the invention as described herein and herein after claimed.

EXAMPLES

Example 1

PREPARATION OF DIHYDROXY-SILICON PHTHALOCYANINE (Pc-Si(OH)$_2$)

Dichlorosilicon phthalocyanine (259 mg) (Aldrich Chemical Co. #28,776-8) was refluxed with stirring in a mixture of 10 ml concentrated ammonium hydroxide and 10 ml pyridine for about 14 hours. Escape of ammonia gas was minimized by sealing off the top of the reflux condenser with a rubber balloon.

The reaction mixture was cooled, diluted to 40 ml with water and centrifuged. The sediment was washed by resuspension in 40 ml water and again centrifuged. In order to sediment the dye in the third water wash, a small amount of ammonium formate was added to promote flocculation. The washed moist residue was dried in vacuo.

Example 2

SULFONATION OF DIHYDROXY SILICON PHTHALOCYANINE

A total of 800 µl chlorosulfonic acid in two different portions was added to 23 mg dihydroxysilicon phthalocyamine. The mixture was stirred constantly while being maintained at a temperature of 110–115° C. for three hours. At this time the reaction mixture was cooled and cautiously added in small portions to ice. The resulting dye solution was saturated with solid sodium chloride; the salted-out dye was removed by centrifugation. The resulting sediment was dried in vacuo to give 16 mg of sulfonated Pc-Si(OH)$_2$.

Example 3

COUPLING OF POLYETHYLENE GLYCOL TO SULFONATED Pc-Si-(OH)$_2$.

A mixture of 2 mg of sulfonated Pc-Si(OH)$_2$ and 300 μl polyethyleneglycol (average molecular weight 300) was held at a temperature of about 185–200° C. for thirty minutes. The reaction mixture quickly became dark green upon heating and when cooled, after the thirty minute period was used directly for characterization of spectroscopic and solution properties.

A small amount of the reaction mixture (about 1 drop) affording an appropriate level of fluorescence intensity was diluted in DMF and 5 μl of this solution was added to 2 ml of SAP in a fluorescence cuvette. The transient state fluorescence was measured at an excitation wavelength of 694 nm with no emission filter. After an initial trace in SAP, 100 μl of 5% HSA was added and the fluorescence was remeasured. This was followed by the addition of 100 μl of human serum and a final measurement of fluorescence. FIGS. 1A (SAP), 1B (SAP+HSA) and 1C (SAP+HSA+serum) demonstrate that no significant differences in the fluorescence intensity, decay time or polarization were observed in the curves obtained. This result indicated that the sulfonated Pc-PEG compound obtained exhibits no detectable binding to serum components.

Example 4

DEMONSTRATION OF STAGES IN THE REACTION BETWEEN PcSi(OH$_2$) and PEG.

A small amount (<1 mg) of PcSi(OH)$_2$ was mixed with about 300 μl PEG 300 (Aldrich #20237-1) in a 12×75 mm test tube. The mixture was shaken by hand to give a turbid blue suspension and was then placed in a sand bath at 185° C. for 1 minute, then removed and allowed to cool. The suspension had cleared somewhat and was still blue. An initial sample (Early Blue Stage) was removed. Heating was then continued for an additional 10 minutes at 183–185° C. at which time the mixture was nearly clear and had a blue-green color (Blue Green Product). Samples of the two stages (10 μl each) were diluted with 1 ml DMF each and then 60 μl of these solutions were added to 3 ml portions of either DMF or SAP for fluorescence measurements. The results are shown in FIGS. 4A and 4B (Early Blue Stage) and 5A and 5B (Blue Green product). For the early blue stage the fluorescence signal in SAP was only ⅙ as great as that in DMF while for the Blue Green Product the entire time course of the transient fluorescence in the two solvents was substantially identical.

These results are in harmony with the concept that in the Early Blue Stage the central Si moiety of the silicon phthalocyanine molecule had combined with only one PEG molecule leaving the planar dye molecule unprotected on one side, while in the Blue Green Stage the Si moiety had combined with two PEG molecules, thus fully protecting the dye structure from solvent effects. Such a structure might be symbolized appropriately by PcSi(PEG)$_2$.

Example 5

ABSORBANCE OF PcSi(PEG-Me, 350)$_2$ IN DMF AND IN SAP

In a 12×75 mm test tube, 0.8 mg PcSi(OH)$_2$ was mixed on a vortex mixer with 1 ml PEG-Me, 350 (Aldrich #20247-9) and 100 μl quinoline (Aldrich #24157-1). The mixture was placed in a sand bath at 180° C. and heated over a period of 1 hour to 220° and for an additional 30 minutes at 220°. At this point the solution was clear and of a deep green color.

A sample (100 μl) was diluted with 200 μl SAP and centrifuged at 10,000 g for 40 minutes. No visible sediment was detected and 60 μl of the supernatant fluid was diluted in 3 ml DMF or SAP. Absorbance scans in two solvents showed that the integrated absorbances are nearly identical with maxima separated by only 7 nm.

FIGS. 3A and 3B depict the visible and near-infrared absorbance in DMF and SAP.

These measurements support the position that the material formed in the reaction corresponded to PcSi(PEG)$_2$. The pronounced green color arising on long heating did not contribute significantly to absorption in the spectral region shown in FIG. 3A and 3B but only at much lower wavelengths (350–400 nm) and it is only the eye that perceives the mixture of blue and red absorbance as green. As shown in Example 4, the condensation reaction proceeded very rapidly even in the absence of any catalyst and probably has gone to completion well before the solution was noticeably green. The present example was of additional significance in that no functional groups are present on the Pc ring and only one active group (—OH) was present on each molecule of PEG. These conditions considered in conjunction with the large molar excess of PEG in the reaction mixture strongly support the formulation of PcSi (PEG-Me)$_2$ for the product absorbing in the 680 nm region.

Example 6

EFFECT ON FLUORESCENCE BEHAVIOR OF PcSi(PEG-Me)$_2$ CAUSED BY SERUM COMPONENTS

FIGS. 2A and 2B demonstrate that the fluorescence of PcSi (PEG-Me)$_2$ in SAP was unaffected by serum in concentrations prevalent in immunoassays.

The DMF solution of PcSi(PEG-Me)$_2$ utilized in Example 5 for the measurement of absorbance was further diluted (3 μl+3 ml SAP) for the present experiments.

Transient state fluorescence of the solution was measured with or without the addition of 100 μl of human serum (to give a total volume of 3.1 ml). The results are shown in FIGS. 2A and 2B. The fluorescence intensity, polarization and decay time were nearly identical in the two samples which indicated a lack of binding of serum components in SAP. However, if the medium was made very non-chaotropic so as to accentuate hydrophobic interactions, binding may then be observed. Samples of sulfonated silicon phthalocyanine without the PEG ligands in aqueous solution will show changes in both fluorescence intensity and polarization where serum is added.

Example 7

BEHAVIOR OF PcSi(PEG 300)$_2$ IN GEL FILTRATION

A column of P-30 Biogel (Bio Rad Laboratories) which had a fractionation range of 2,500 to 40K daltons was made in SAP. Column volume was 5.1 ml and length was 17.5 cm. The void volume was found to be 1.5 ml for blue dextran which came through in 0.61 ml when 100 μl was applied. When 100 μl of sulfonated Pc-Si(PEG)$_2$ as used in Example 3 was applied to the column, the breakthrough was out 3.48 ml and practically all the material was contained in 0.77 ml.

Since the dye breakthrough was not until 2.3 times the void volume, it indicated that the dye was not aggregated even at concentrations (i.e. color) that can be seen by the unaided eye.

Example 8

BEHAVIOR OF SULFONATED PcSi(PEG 300)$_2$ ON FILTERS OF KNOWN POROSITY

To 495 μl of modified Dorsett buffer (an aqueous solution containing 0.14M NaCl, 0.0025M KCl, 0.0015M KH$_2$PO$_4$, 0.010M Na$_2$HPO$_4$, 0.001M NaN$_3$ and 0.05% Tween 20) was added 5 μl of sulfonated PcSi(PEG)$_2$ (as used in Example 3). To a filter which would retain molecules of 30,000 daltons or more (Millipore Corp, Ultrafree Mc, 30,000 NMWL) was added 420 μl of the buffered PcSi (PEG)$_2$ solution. The filter assembly was centrifuged for 40 minutes at 7000 g.

Steady state fluorescence measurements made in a digital, photon-counting fluorescence polarometer with excitation at 700 nm demonstrated that 59%. of the dye was recovered in the filtrate. Three other buffers tested in the same format allowed only very small fractions of the dye to pass into the filtrate. These results were probably attributable to adsorption on the filter surface which in the case of modified Dorsett buffer was possibly prevented by inclusion of Tween 20.

Example 9

PREPARATION OF A WATER-SOLUBLE BIS-POLYETHYLENEGLYCOL SILICON PHTHALOCYANINE

Chloropropyldimethylchlorosilane was purchased from Petrarch Systems.

Dihydroxysilicon phthalocyanine (0.16 mmol), imidazole (0.7 mmol), and dry DMF (1 ml) were placed in a flask and stirred at 20° C. while chloropropyldimethylchlorosilane (0.7 mmol) was added dropwise, taking care to exclude atmospheric moisture. Stirring at 20° C. was continued for 20 hours.

At this time, solvent was removed under reduced pressure, and the product applied to a silica gel chromatography column. Elution with CH$_2$Cl$_2$-hexane (1:1) afforded a single major colored fraction, SiPc[OSi(CH$_3$)$_2$CH$_2$CH$_2$CH$_2$Cl]$_2$ (compound I).

NMR spectra were recorded on a General Electric QE-300 Spectrometer. NMR (CDCl$_3$): δ 9.65 (m, aromatic, 4H), δ 8.45 (m, aromatic, 4H), δ 2.1 (t, CH$_2$—Cl, 2H), δ −0.85 (m, CH$_2$, 2H), δ −2.09 (m, CH$_2$—Si, 2H), δ −2.85 (s, CH$_3$, 6H).

A. Compound I (0.01 mmol) was placed in a flask with amine-terminated polyethyleneglycol, MW 2000 (0.2 mmol), sodium iodide (0.01 mmol) and DMF (1 ml), and the mixture was heated and stirred at 90° C. for 15 hours.

Removal of solvent under reduced pressure afforded a viscous blue liquid which was purified by chromatography. This product, SiPc[OSi(CH$_3$)$_2$CH$_2$CH$_2$CH$_2$NH—PEG]$_2$, was highly water soluble and exhibited strong fluorescence in aqueous solution. The fluorescence of this material as a solution in a biological buffer was not affected by the addition of human serum albumin (to a final concentration of 3 weight volume %)

B. Compound I (0.01 mmol) is placed in a flask with amine-terminated polyethyleneglycol, MW 600 (0.2 mmol), sodium iodide (0.01 mmol) and DMF (1 ml), and the mixture is heated and stirred at 90° C. for about 15 hours.

Removal of solvent under reduced pressure affords a viscous blue liquid which is purified by chromatography.

Example 10

PREPARATION OF THE SULFONYLCHLORIDE OF SILICON PHTHALOCYANINE

To 0.91 g dichlorosilicon phthalocyanine in a flask with a reflux condenser, drying tube and stirring bar was added 8.6 ml chlorosulfonic acid. The mixture was heated with stirring to 100–115° C. After 3.5 hours, the mixture was allowed to cool overnight. Conversion to the sulfonyl chloride was carried out by adding 6 ml thionyl chloride and then refluxing the resulting mixture for 1.5 hours. The mixture was cooled and added slowly to ice. The aqueous suspension was filtered and the solid was washed thoroughly with water and finally dried in vacuo over P$_2$O$_5$ to give 1.41 g of the above-identified product as a dry solid.

Example 11

MAGNESIUM TETRABENZOTRIAZAPORPHYRIN (MgTBTAP)MAGNESIUM 27-PHENYLTETRABENZOTRIAZAPORPHYRIN Mg 27-PhTBTAP)MAGNESIUM 27-(P-METHYLPHENYL) TETRABENZOTRIAZAPORPHYRIN (Mg 27-p-MePhTBTAP)

The synthesis of magnesium tetrabenzotriazaporpyrhin was first reported by Linstead in 1939 (Ref. 6). This dye was prepared by treating 1:1 equivalent of 1,2-dicyanobenzene with MeMgI in ether. After removal of ether, the intermediate was heated at 200° C. to give MgTBTAP. We found that during the heating process, the presence of high boiling solvent such as 1,2,3,4-tetrahydronaphthalene in the reaction mixture was essential to increasing the yield of MgTBTAP. We, therefore, modified the procedures.

A. Magnesium Tetrabenzotriazaporphyrin (MQTBTAP)

A solution of 27 ml of 3M MeMgI was added to a stirred mixture of 10.5 g 1,2-dicyanobenzene and 250 ml ether. The liquid immediately turned light brown. Within five minutes, a dark brown mass began to separate and the ether began to boil gently. The reaction was allowed to proceed without cooling and the reaction vessel was kept open allowing ether to evaporate. After ½ hour, the reaction ceased and the remainder of the ether was removed on a hot water bath. To the dry residue were added 20 ml 1,2,3,4-tetrahydronaphthalene. The mixture was placed in an oil bath preheated to 190°. After 5 minutes, the temperature reached 200°. Water was added dropwise and an evolution of white fumes took place. A total of 20 ml water were added over a period of 20 minutes. Heating was continued at 200° for ½ hour. After cooling to room temperature, the dark solid was crushed and repeatedly extracted with a mixture of EtOH and concentrated HCl (9:1) until the extracts were no longer yellow brown. The residue was washed with acetone and dried in a vacuum desiccator overnight. Yield was 4.35 g.

B. Magnesium 27-Phenyltetrabenzotriazaporphyrin (Mg 27-PhTBTAP)

In the same manner as described above, 27-PhTBTAP was prepared. From 4.84 g 1,2-dicyanobenzene and 40 ml 1M benzylmagnesium chloride, 7.53 g crude product were obtained. A considerable amount of magnesium 27-phenyl-tetrabenzdiazaporphyrin (Mg 27-PhTBDAP) was formed as a side product in this synthesis. In addition, some magnesium phthalocyanine (MgPc) was also formed. The crude Mg 27-PhTBTAP can be purified on a $SiO_2$ column according to the procedures described by Leznoff. [Ref. 7]

C. Magnesium 27-(p-Methylphenyl) tetrabenzotriazaporphyrin Mg 27-p-MePhTBTAP

When Linstead's procedures or our modified procedures for the synthesis of MgTBTAP were followed, only a trace of 27-p-MePhTBTAP was formed. The major product was MgPc. Therefore, the procedures were further modified.

In a three necked round-bottom flask, fitted with a nitrogen inlet, a drying tube, and a dropping funnel, were placed 21.5 g 1,2-dicyanobenzene and 140 ml THF. Under a nitrogen blanket, the mixture was stirred for a few minutes until all solid was in solution. A solution of 216 ml 0.77M p-methylbenzylmagnesium chloride was added dropwise over a period of 2 hours. The liquid turned light yellow and then yellow green after a few drops of the Gringnard reagent were added. The color turned pink purple and finally dark purple upon addition of more Gringnard reagent. After stirring at room temperature for an additional ½ hour, the solvent was removed under reduced pressure. To the residue was added 87 ml 1,2,3,4-tetrahydronaphthalene. The mixture was then placed in a preheated oil bath (205° C.). After 1 hour at 205° C., water was added in drops at 10–20 minute time intervals. A total of 16 ml water was added over an extended 3 hours of heating. The mixture was allowed to cool and then dried under reduced pressure to remove residual water. The residue was then stirred in 200 ml hexane. The precipitate was collected by filtration and repeatedly washed with hexane until the filtrate had no more brown color. After being dried in air, the solid was stirred in 400 ml 1.2M HCl and filtered. The precipitate was washed with water thoroughly and dried in a vacuum desiccator overnight to afford a dark powdery solid. Yield was 24 g. This solid was shown by TLC to contain five compounds, presumably, Mg-27-p-MePhTBTAP, the corresponding diaza and monoaza compounds the prophyrin, and MgPc. The Mg 27-p-MePhTBTAP was the predominant product. The product was isolated and purified on a silica gel column eluting with a mixture of 1560 ml hexane, 642 ml THF, and 312 ml acetone. A total of 20 fractions were collected. Fractions 5–10 contained mostly the triaza-compound dye and some diaza- and monoaza-compound. Removal of solvent afforded 5.2 g dark solid. This solid was further purified on a $SiO_2$ column eluting with 2360 ml solvent mixture of hexane, THF, and acetone in the ratio of 8:2:1. A total of 42 fractions were collected. From these fractions, 2.63 g semi-pure Mg 27-p-MePhTBTAP were obtained. Recrystallization from acetone afforded a pure Mg 27-p-MePhTBTAP. Yield was 1.12 g.

Example 12

TETRABENZOTRIAZAPORPHYRIN (TBTAP) 27-PHENYLTETRABENZOTRIAZAPORPHYRIN (27-PhTBTAP) 27-(p-METHYLPHENYL) TETRABENZOTRIAZAPORPHYRIN (27-p-MePhTBTAP)

A. Tetrabenzotriazaporphyrin

Following Linstead's procedures, the crude MgTBTAP, 0.35 g, was stirred with 20 ml concentrated $H_2SO_4$ at room temperature. After ½ hour, the yellow-brown solution was cautiously added in small portions to ice water and the mixture was centrifuged. The green precipitate was collected and repeatedly washed with water and centrifuged. The residue was then dried in a vacuum desiccator overnight providing a dark blue solid. Yield was 0.24 g.

B. 27-(p-Methylphenyl)tetrabenzotriazaporphyrin (27-p-MePhTBTAP)

To a solution of 0.23 g 27-p-MePhTBTAP in 12 ml DMF was added with stirring 1.2 ml concentrated HCl. After ½ hour, 1.27 ml pyridine was added to neutralize the acid. The mixture was poured into 75 ml water and then kept in a freezer for ½ hour. The precipitate was collected, washed with water and then dried in a vacuum desiccator overnight affording a dark solid. The solid was purified by recrystallizing from a mixture of 20 ml acetone and 30 ml MeOH. Yield was 0.20 g.

C. 27- Phenyltetrabenzotriazaporphyrin (27-PhTBTAP)

The same procedures as described above for the demetalation of Mg 27-p-MePhTBTAP was applied to Mg 27-PhTBTAP and a metal free 27-PhTBTAP was obtained.

Example 13

SILICON TETRABENZOTRIAZAPORPHYRIN DICHLORIDE ($SiCl_2TBTAP$) SILICON 27-PHENYLTETRABENZOTRIAZAPORPHYRIN DICHLORIDE ($SiCl_2$27-PhTBTAP)

SILICON 27-(P-METHYLPHENYL) TETRABENZOTRIAZAPORPHYRIN DICHLORIDE ($SiCl_2$27-p-MePhTBTAP)

A. Silicon Tetrabenzotriazaporphyrin Dichloride ($SiCl_2TBTAP$)

In a 25 ml round-bottomed flask, fitted with a drying tube and a condenser, were placed 151 mg TBTAP. 15 ml THF were added. The mixture was stirred under a nitrogen blanket and 2.5 ml 1.5M lithium diisopropylamide were added. The mixture turned purple immediately. After 20 minutes, 2.5 ml $SiCl_4$ were added and the mixture was then heated under reflux. After 1 hour, the solvent and the excess $SiCl_4$ were removed under reduced pressure. The dry residue was extracted with 10 ml THF. The THF extract was evaporated to dryness and the residue was repeatedly washed with water until the washing were nearly colorless. The residue was dried providing 55 mg dark solid. Absorption spectrum showed $\lambda$ max 648, 669 and 693. Addition of $NH_4OH$ shifted $\lambda$ max to 647.1 and 668.8. The original residue left from the THF extract was extracted with DMF 8×6 ml. Fractions containing $\lambda$ max 647.1, 670.5 and 692.2 were combined. Removal of solvent afforded 38 mg dark solid. The solid was redissolved in DMF and treated with $NH_4OH$. The $\lambda$ max shifted to 647.1 and 668.8. After removal of solvent and $NH_2OH$, 35 mg dark solid were recovered. The residue left from the DMF extract was further extracted with hot DMF 12×2 ml. Absorption spectrum showed $\lambda$ max 670.5 and 693.9. Addition of $NH_4OH$ shifted λ max to 647.1 and 668.8. Removal of DMF afforded 10 mg dark solid. The combined yield was 90 mg. It seems that the dye in the protonated form had λ max 670.5 and 693.9. When deprotonated, its λ max shifted to 647.1 and 668.8. Subsequently, we have found that demetallation may take place if the removal of $SiCl_4$ is not complete. To prevent demetallation in the workup of the reaction mixture, a small amount, e.g. about 0.4 moles of pyridine per mole $SiCl_4$ used were added after removal of the $SiCl_4$ and before any contact with water.

B. Silicon 27-Phenyltetrabenzotriazaporphyrin Dichloride ($SiCl_2$27-PhTBTAP) and Silicon 27-(p-Methylphenyl)tetrabenzotriazaporphyrin Dichloride ($SiCl_2$27-p-MePhTBTAP)

In the same manner as described above, these two dichloro silicon triaza compounds were prepared from their respective metal-free forms using lithium diisopropylamide and $SiCl_4$ in THF.

Example 14

TETRABENZOTRIAZAPORPHYRIN SULFONYL CHLORIDE [TBTAP($SO_2Cl)_x$]27-(PMETHYLPHENYL) TETRABENZOTRIAZAPORPHYRIN SULFONYL CHLORIDE [27-p-MePhTBTAP ($SO_2Cl$)]

27-PHENYL TETRABENZTRIAZAPORPHIN SULFONYL CHLORIDE [27-PhTBTAP ($SO_2Cl$)]

A. Tetrabenztriazoaporphyrin Sulfonyl Chloride [TBTAP ($SO_2Cl)_x$]

In a 25 ml round-bottomed flask, fitted with a condenser and a drying tube, were placed 0.401 g MgTBTAP and 10 ml $ClSO_3H$. The mixture was stirred and heated at 80–90°. After 3 hours, 5 ml $SOCl_2$ were added. Heating and stirring were extended for 3 hours. The mixture after being cooled to room temperature was added in small portions to ice. The green mixture was centrifuged the residue was repeatedly washed with saturated NaCl and filtered. The precipitate was finally washed with ice water and dried in a vacuum desiccator leaving a dark solid. Yield was 0.168 g.

B. 27-(p-Methylphenyl)tetrabenzoytriazaporphyrin Sulfonyl Chloride [27-p-MePhTBTAP($SO_2Cl$)]

To sulfonate the 27-p-Methylphenyl nucleus selectively, the above procedures were modified. In a 25 ml round-bottomed flask, fitted with a condenser and a drying tube, were placed 0.265 g Mg 27-p-MePhTBTAP, 6 ml $ClSO_3H$, and 1.5 $SOCl_2$. The mixture was stirred at 42–46° overnight (16 hours) and then worked up according to the procedures described above. Yield was 0.296 g.

C. 27-Phenyltetrabenzotriazaporphyrin Sulfonyl Chloride [27-PhTBTAP($SO_2Cl$)]

Following the modified procedures described above, Mg-27-PhTBTAP was sulfonated to give the corresponding Mg 27-PhTBTAP($SO_2Cl$).

Example 15

SILICON TETRABENZOTRIAZAPORPHYRIN DIHYDROXIDE [Si(OH)$_2$TBTAP]

Joyner's procedure for converting $PcSiCl_2$ into PcSi(OH)$_2$ was followed. [Ref. 7]

In a 25 ml round-bottomed flask, fitted with a condenser and a balloon, were placed 33 mg $SiCl_2$TBTAP, 3 ml $NH_4OH$, and 3 ml pyridine. The mixture was heated under reflux overnight. After being cooled, the mixture was evaporated under reduced pressure to dryness. The residue was stirred in a small amount of water and the mixture was centrifuged. The final residue was dried leaving a dark solid. Yield was 32 mg.

Example 16

SILICON TETRABENZOTRIAZAPORPHYRIN BIS-PHENYLPOLYETHYLENE GLYCOL SiTBTAP-(O-PhPEG)$_2$.

A trace of $SiCl_2$TBTAP was mixed with 150 mg hydroxyphenylpolyethylene glycol (Fw=2000) and 20 µl quinoline. The mixture was heated in a sand bath at 195° for 5 min. After cooling, the mixture was diluted in DMF. The DMF solution was further diluted in $H_2O$. The aqueous solution was centrifuged. A green supernatant was obtained. The absorption spectrum of this compound was very similar in DMF or aqueous buffer while the intensity of the fluorescence emission was somewhat greater in aqueous buffer than in DMF.

Example 17

LOW TEMPERATURE SULFONATION OF DIHYDROXYSILICON PHTHALOCYANINE

Pc-Si(OH)$_2$, 741 mg was added to 14.8 ml $ClSO_3H$ and stirred at 70° C. for a few minutes to dissolve. Ten ml $SOCl_2$ was added and the mixture was stirred and maintained at 80° C. for 6.5 hours. The reaction mixture was then cooled to −15° C. and added to precooled ice. Approximately 600 ml of loosely packed ice cubes were necessary to absorb the heat generated. The suspension of dye was centrifuged at about 1000×g and the sediment was suspended in $H_2O$ containing a small amount of NaCl and filtered on a Buchner funnel and washed in situ with $H_2O$. The product was dried in vacuo.

Example 18

β-ALANINE DERIVATIVE OF SULFONATED PHTHALOCYANINE

β-Alanine, 514 mg and $Na_2CO_3H_2O$, 750 mg were dissolved in 6 ml $H_2O$. With stirring 103 mg of sulfonated PcSi(OH)$_2$ (prepared as in Example 17) was added. The mixture was stirred and maintained at 70°–80° C. for 2.5 hours and then stirred at room temperature overnight. The reaction mixture was acidified with dilute HCl and centrifuged. The sediment was stirred in NaCl solution and recentrifuged. The sediment was dissolved in MeOH and dried in vacuo. The dry material was redissolved in MeOH and filtered. The filtrate was mixed with 5 g silica (Silica Gel 60-EM Products) and dried in vacuo. The solid was added to a silica gel column and developed with $CH_2Cl_2$ until the effluent was colorless and the dye was then eluted with a gradient of MeOH in $CH_2Cl_2$. Fractions were examined by TLC, and were selected by content of the main component, pooled, and dried in vacuo. This material was further purified by preparative TLC on silica in $CH_2Cl_2$ and MeOH (6:1).

Example 19

DIGOXIN CONJUGATE OF PHTHALOCYANINE (Pc-DIG)

The β-alanine derivative of sulfonated phthalocyanine (prepared as in Example 18), 3.4 µg was dissolved in 400 µl DMF. To this solution were added 100 µl of pyridine, 22 µl HOBT (57 mg/ml in DMF) and 150 µl 1-ethyl-3-(3-dimethylaminopropyl)-carbodiimide (EDAC) (27 mg/ml in DMF). The resulting solution was added to a solution of 3.8 mg 3-amino digoxigin in 100 µl DMF; the resulting mixture was kept at room temperature overnight. The digoxin conjugate was purified by TLC (#5737-7, EM Products), developed with $CH_2Cl_2$ and MeOH (6:1) and later with $CH_2Cl_2$ and MeOH (6:5). The main band ($R_f$-0.5) was extracted with MeOH and dried in vacuo.

Example 20

PEG-PHENOL 750

To a mixture of amine terminated PEG, 836 mg, dissolved in 2 ml $CH_2Cl_2$, 186 mg 3-(4-hydroxyphenyl)propionic acid N-hydroxysuccinimide was added. The resulting mixture was kept at room temperature overnight. The solvent was evaporated in vacuo.

Example 21

Pc-DIG-PEG PHENOL CONJUGATE

Pc-DIG (1 mg) was mixed with 250 mg PEG Phenol 750 and heated at 188–198° C. for 5 minutes. After cooling, the melt was dissolved in DMF for use in an immunoassay. In a test for binding activity to anti-digoxin monitored by transient state polarized fluorescence, a trace amount of the conjugate was dissolved in 2 ml SAP containing 50 µl of human serum and 2 ml of an antibody preparation. A change of 0.056 in polarization was obtained over that in the control with no antibody.

Example 22

MEASUREMENTS OF TRANSIENT STATE FLUORESCENCE

Transient state fluorescence emission was measured as follows: A tunable dye laser was used to excite the sample with a pulse of light. The laser consisted of a nitrogen laser generating 50 KW peak pulse power and a dye laser module which produced 5 KW peak pulse power. The dye laser was tunable by orientation of a grating by adjustment of a micrometer scaled in nm and by using the appropriate laser dye for the wavelength range required for the experiments. Total pulse time was approximately 600 ps. A small portion (less than 10% of the beam) was split off to a high speed Hammamatsu photodiode to determine the time of the pulse and to obtain a reading of the pulse power. The fluorescence signal was monitored at 90° to the excitation direction. A filter was used to remove the majority of the laser pulse light for turbid samples. A lens was used to focus the fluorescent signal onto the PMT photocathode. A rotatable polarizer with 2 positions for parallel and perpendicular orientation relative to the laser polarization was located just before the PMT. The PMT was a gateable microchannel plate PMT from Hammamatsu with sensitivity from 400 nm up to 850 nm.

A Tektronix 7912 programmable digitizer was used to capture the fluorescence signal following each pulse of light. The laser pulse, polarizer position, and the digitizer was controlled by computer.

To measure transient state fluorescence emission, the user sets up the number of pulses required for the experiment, and starts the experiment. The computer then triggered the laser whose pulse was detected by the photodiode. A pulse shaper is used to stretch the 0.5 ns pulse to 100 ns. After the laser pulse had passed through the reaction cells, the PMT was gated on within 2 ns. This increased its sensitivity by 10,000 fold. The gate from the photodiode also activated the digitizer gate which then captured the next 20 ns of current produced by the PMT.

In practice, information was acquired with the polarizer parallel to the excitation source, then the polarizer was reoriented and data was acquired perpendicular to the direction of the polarization of the excitation source. The data for the number of pulses selected was averaged for both polarizer orientations and displayed on the monitor. The data can then be stored, printed, and analyzed to determine the fluorescent decay time, decay of polarization, and the total intensity. Data can be collected from solutions without the fluorescent dyes to obtain blanks which can be subtracted from the fluorescent decay curves of the dyes.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are within the following claims.

BIBLIOGRAPHY

1. Kricka, J. J.; *Ligand-Binder Assays; Labels and Analytical Strategies*; pages 15–51; Marcel Dekker, Inc., New York, N.Y. (1985).

2. Moser, F.; *Phthalocyanine Compounds*; Reinhold Publishing Co., New York (1963).

3. Wilkinson, G. (editor); *Comprehensive Coordination Chemistry*; Volume 2, pages 813–898; Pergamon Press, New York (1987).

4. Hanack, M., et al.; "Synthesis and Properties of a New Kind of One-Dimensional Conductor", *Journal of Organometallic Chemistry* 204:315–325 (1981).

5. Lezhoff, C. C. and Lever, A. S. P. (editors); *Phthalocyanines: Properties and Applications*; VCH Publishers, Inc., New York (1989).

6. Barrett, P. A., Linstead, R. P. and Tuey, G. A. P., *J. Chem. Soc. (London)*, 1809–1820 (1939).

7. Leznoff, C. C. and McKeown, N. B., *J. Org. Chem.* 55:2186–2190 (1990).

8. Joyner, R. D. and Kenney, M. E., *Inorg. Chem.* 1:236–238 (1962).

We claim:

1. A detectably labeled marker component which comprises a substantially planar fluorophore moiety coupled to two solubilizing polyoxyhydrocarbyl moieties, one located on either side of the plane of the fluorophore moiety, wherein said polyoxyhydrocarbyl moieties are selected from the group consisting of water soluble carbohydrates and water soluble carbohydrate derivatives and wherein said fluorophore moiety comprises a macrocycle multidentate ligand coordinated to a central atom, wherein said macrocycle ligand is selected from the group consisting of a porphyrin derivative, a porphyrin derivative having one or more bridging carbons replaced by nitrogen, a corrin derivative, a sapphyrin derivative and a porphycene derivative, and wherein each of said polyoxyhydrocarbyl moieties has a molecular weight of about 200 to about 20,000.

2. A marker component according to claim 1 wherein one of the two solubilizing polyoxyhydrocarbyl moieties is linked on either side of the macrocyclic ligand to the central atom.

3. A marker component according to claim 2 wherein the two polyoxyhydrocarbyl moieties comprise axial ligands which coordinate to the central atom.

4. A marker component according to claim 3 wherein said central atom is capable of forming octahedral coordination complexes.

5. A marker component according to claim 4 wherein said macrocyclic ligand has a conjugated π-electron system.

6. A marker component according to claim 1 wherein said central atom is selected from silicon, germanium, phosphorus and tin.

7. A marker component according to claim 1 wherein said macrocycle comprises a porphyrin derivative wherein from 1 to 4 of the bridging carbon atoms is replaced by nitrogen.

8. A marker component according to claim 1 wherein said macrocy comprises a tetrabenzotriazaporphyrin derivative.

9. A marker component according to claim 8 wherein said macrocycle is selected from tetrabenzotriazaporphyrin, 27-phenyltetrabenzotriazaporphyrin, and 27-(p-methylphenyl)tetrabenzotriazaporphyrin.

10. A marker component according to claim 8 wherein the central atom is silicon.

11. A marker component according to claim 7 wherein said macrocyclic ligand has a low degree of symmetry so as to enhance the polarization of emission parallel to polarization of absorption.

12. A marker component according to claim 11 wherein said central atom is silicon or germanium.

13. A marker component according to claim 12 wherein said macrocyclic ligand has a lower symmetry than $D_{4h}$.

14. A marker component according to claim 13 wherein said macrocyclic ligand has at least one fused aromatic ring.

15. A marker component according to claim 14 wherein said macrocyclic ligand comprises a porphyrin derivative wherein 1 to 3 of the bridging carbon atoms is replaced by nitrogen.

16. A marker component according to claim 14 wherein said macrocyclic ligand comprises a phthalocyanine derivative.

17. A marker component according to claim 16 wherein said macrocycle comprises a tetrabenzotriazaporphyrin derivative.

18. A marker component according to claim 14 wherein said central atom comprises silicon.

19. A marker component according claim 14 wherein said central atom comprises germanium.

20. A fluorescent probe which comprises a marker component according to claim 1 linked to one member of a specific binding pair.

21. A fluorescent probe which comprises a marker component according to claim 18 it linked to one member of a specific binding pair.

22. A fluorescent probe according to claim 21 wherein said member of a specific binding pair comprises a digoxin derivative.

23. A fluorescent probe according to claim 20 wherein said member of a specific binding pair has at least one sterically tolerant marker component attachment site capable of permitting said probe to form a specific binding pair.

24. A detectably labeled marker component which comprises a fluorophore moiety coupled to two solubilizing polyoxyhydrocarbyl moieties, which in the presence of serum components in aqueous solution is characterized by transient state fluorescence emission having parallel and perpendicular components of substantially the same intensities as without serum, wherein said polyoxyhydrocarbyl moieties are selected from water soluble carbohydrates and water soluble carbohydrate derivatives and wherein said fluorophore moiety comprises a macrocycle multidentate ligand coordinated to a central atom, wherein said macrocycle ligand is selected from the group consisting of a porphyrin derivative, a porphyrin derivative having one or more bridging carbons replaced by nitrogen, a corrin derivative, a sapphyrin derivative and a porphycene derivative, and wherein each of said polyoxyhydrocarbyl moieties has a molecular weight of about 200 to about 20,000.

25. A marker component according to claim 24 wherein said fluorophore moiety comprises a tetrabenzotriazaporphyrin derivative.

26. A marker component according to claim 24 wherein said fluorophore moiety comprises a phthalocyanine derivative.

27. A fluorescent probe which comprises a marker component according to claim 24 linked to one member of a specific binding pair.

28. A fluorescent probe according to claim 27 wherein said member of a specific binding pair has at least one sterically tolerant marker component attachment site capable of permitting said probe to form a specific binding pair.

29. A marker component according to claim 1 wherein said water soluble carbohydrates are selected from the group consisting of glucose, sucrose, and maltotriose.

30. A marker component according to claim 1 wherein said water soluble carbohydrate derivatives are selected from the group consisting of gluconic acid, mannitol, and oligosaccharides.

31. A marker component according to claim 1, wherein said fluorophore moiety is a naphthalocyanine or a naphthalocyanine derivative.

* * * * *